(12) United States Patent
Kojo et al.

(10) Patent No.: US 6,895,649 B2
(45) Date of Patent: May 24, 2005

(54) ARTICLE PRODUCTION METHOD

(75) Inventors: Kenzo Kojo, Osaka (JP); Kazutoshi Makimura, Osaka (JP); Satoshi Tanaka, Osaka (JP)

(73) Assignee: Zuiko Corporation, Osaka (JP)

( * ) Notice: Subject to any disclaimer, the term of this patent is extended or adjusted under 35 U.S.C. 154(b) by 299 days.

(21) Appl. No.: 10/223,983

(22) Filed: Aug. 20, 2002

(65) Prior Publication Data
US 2003/0047273 A1 Mar. 13, 2003

(30) Foreign Application Priority Data
Aug. 29, 2001 (JP) .............................. 2001-258987

(51) Int. Cl.[7] .................. B23Q 17/00; B21D 39/03; B23P 9/00; B23P 13/04
(52) U.S. Cl. .................. 29/407.01; 29/430; 29/445; 29/557
(58) Field of Search .......... 29/407.01, 407.1, 29/428, 429, 430, 439, 445, 450, 469, 557, 588; 156/250, 256

(56) References Cited

U.S. PATENT DOCUMENTS

| | | | |
|---|---|---|---|
| 4,617,082 A | 10/1986 | Oshefsky et al. | |
| 6,109,419 A | 8/2000 | Spatafora et al. | |
| 6,264,780 B1 | * 7/2001 | Iwanaga et al. | ............ 156/136 |

FOREIGN PATENT DOCUMENTS

EP    1162162 A1    12/2001

* cited by examiner

Primary Examiner—John C. Hong
(74) Attorney, Agent, or Firm—Renner, Otto, Boisselle & Sklar, LLP

(57) ABSTRACT

The production method for producing an article, comprises the step of rotating a rotating member so as to machine a semi-finished product with a machining section included in the rotating member. A circumferential velocity of the rotating member can be changed according to a size of the semi-finished product during one cycle in which the semi-finished product is machined.

57 Claims, 18 Drawing Sheets

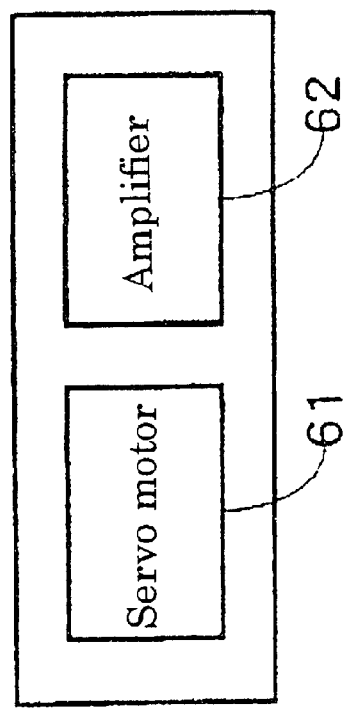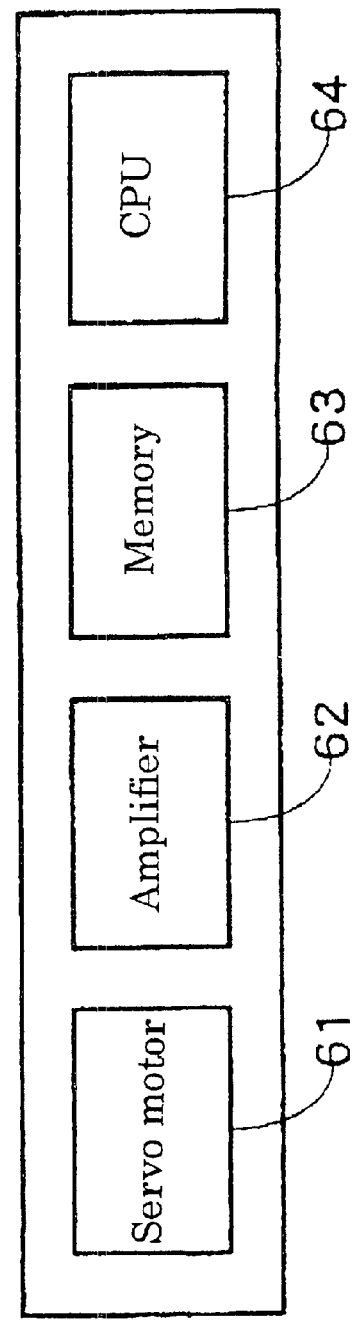
FIG. 8C
FIG. 8D

ARTICLE PRODUCTION METHOD

BACKGROUND OF THE INVENTION

1. Field of the Invention

The present invention relates to an article production method and an article production apparatus for producing articles of different sizes, and more particularly to a production method and a production apparatus for producing disposable pants, such as paper diapers, incontinence pants and sanitary pants, and disposable worn articles such as sanitary napkins.

2. Description of the Related Art

U.S. Pat. No. 3,828,367 discloses a method for producing disposable pants. Generally, there may be a number of sizes, e.g., size S, size M and size L, of disposable pants, etc., even for the same product. Since those pants have basically the same configuration, it is possible to produce the pants, etc., of different sizes by a single machine.

However, since the pants, etc., are sized differently according to the respective sizes, some units need to be replaced, thereby reducing the capacity utilization rate. Such a problem occurs similarly with articles other than worn articles.

SUMMARY OF THE INVENTION

Thus, an object of the present invention is to provide a method and an apparatus for producing an article with which the need for replacing units, etc., is eliminated as much as possible. Moreover, another object of the present invention is to realize an adjustment of the position at which a member or a semi-finished product is machined according to an expansion/contraction of the member or the semi-finished product even when producing articles of the same size.

In order to achieve the object, the present invention provides an article production method capable of producing at least an article of a first size and another article of a second size, the method including a machining step of machining a material included in the article or a semi-finished product of the article by the rotation of a rotating member, wherein the circumferential velocity of the rotating member is changed during a cycle of machining process by the rotating member so as to produce the article of the second size.

The present invention may include at least one rotating member, for example a seal roll, a cutter roll, a tape attachment roll, a trim cutter roll or a re-pitching drum.

The present invention may include at least two rotating members, for example a seal roll and a cutter roll, a seal roll and a tape attachment roll, a seal roll and a trim cutter roll, a cutter roll and a tape attachment roll, a cutter roll and a trim cutter roll, a tape attachment roll and a trim cutter roll, a seal roll and a re-pitching, a cutter roll and a re-pitching drum, a tape attachment roll and a re-pitching drum, or a trim cutter roll and a re-pitching drum.

The present invention may include at least three rotating members, for example a seal roll, a cutter roll, and a tape attachment roll; a seal roll, a cutter roll, and a trim cutter roll; a seal roll, tape attachment roll, and a trim cutter roll; a cutter roll, a tape attachment roll, and a trim cutter roll; a seal roll, a cutter roll, and a re-pitching drum; a seal roll, a tape attachment roll, and a re-pitching drum; a seal roll, a trim cutter roll, and a re-pitching drum; a cutter roll, a tape attachment roll, and a re-pitching drum; a cutter roll, a trim cutter roll, and a re-pitching drum; or a tape attachment roll, a trim cutter roll, and a re-pitching drum.

The present invention may include at least four rotating members, for example a seal roll, a cutter roll, a tape attachment roll, and a trim cutter roll; a re-pitching drum, a seal roll, a cutter roll, and a tape attachment roll; a re-pitching drum, a seal roll; a cutter roll, and a trim cutter roll; a re-pitching drum, a seal roll, a tape attachment roll, and a trim cutter roll; or a re-pitching drum, a cutter roll, a tape attachment roll, and a trim cutter roll.

The present invention may include at least five rotating members, for example a seal roll, a re-pitching drum, a seal roll, a cutter roll, a tape attachment roll, and a trim cutter roll.

Furthermore, the production apparatus including the rotating member may include a guide section. The production apparatus including the rotating member may include a laser cutter. The production apparatus including the rotating member may include a water jet cutter. The production apparatus including the rotating member may include a guide unit and a laser cutter. The production apparatus including the rotating member may include a guide unit and a water jet cutter. Moreover, the production apparatus for realizing the production method may include any other machining section.

Moreover, in the present invention, the rotating member may include a roll having one or more machining section for processing a material or a semi-finished product. For example, a roll having a machining section may be the seal roll for sealing a material or a semi-finished product, the cutter roll for cutting an article, the tape attachment roll for attaching a tape on a web, or the like.

BRIEF DESCRIPTION OF THE DRAWINGS

FIG. 8C and FIG. 8D each illustrate an example of a motor module.

DESCRIPTION OF THE PREFERRED EMBODIMENTS

A principle of the present invention will now be described.

In the prior art, a mat cutter unit for cutting a continuous absorbent, etc., is replaced with another mat cutter unit according to the size of an article to be produced. For example, if mats of articles of size L, size M and size S have lengths of L3, L2 and L1, respectively, cutter rolls having circumferences of L3, L2, L1 are used for size L, size M and size S, respectively, wherein the rolls are rotated at a generally constant rotational velocity (number of revolutions/min).

However, it is possible to produce mats of different lengths by changing the velocity at which a cutter roll is rotated.

Figure 1A:
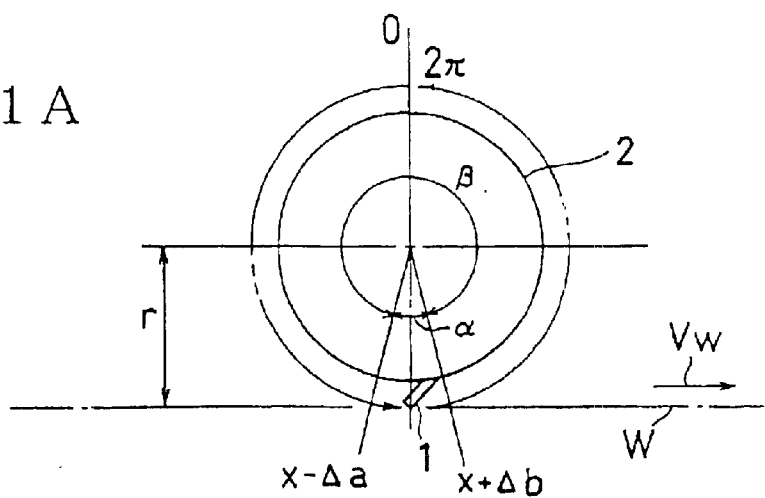
FIG. 1A illustrates an example of a rotating member having a machining section.

FIG. 1A is a diagram illustrating a rotating member 2 having a machining section 1. The rotating member 2 can be rotated so as to machine a material or a semi-finished product (hereinafter referred to collectively as a "semi-finished product") of an article. For example, in a case where the rotating member 2 is a cutter roll with a blade, the rotating member 2 can perform a machining process of cutting a semi-finished product of an article.

For example, a semi-finished product may be machined by the machining section 1 illustrated in FIG. 1A as follows. When the machining section 1 is located in a working area α (x−Δa to x+Δb) shown in FIG. 1A, the circumferential velocity of the machining section 1 (i.e., the circumferential velocity during the machining process) is set to be generally equal to a flow velocity $V_w$ of a web W or greater than the flow velocity $V_w$ by a predetermined proportion. When the machining section 1 is located in a non-working area β (0 to x−Δa, and x+Δb to 2π), the circumferential velocity of the machining section 1 is changed according to the size of the article so that the interval between machining processes performed on the semi-finished product matches with the size of the article.

Note that if an article of size L is produced with a cutter roll for size M by simply reducing the rotational velocity of the cutter roll with the web flow velocity being unchanged, it may be difficult to cut a continuous mat because the circumferential velocity of the blade (machining section) is lower than the web flow velocity V.

Figure 2A:
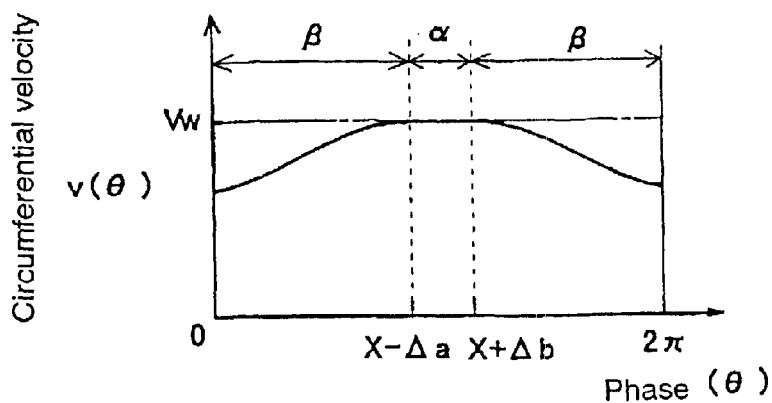
FIG. 2A to FIG. 2C, FIG. 3A and FIG. 3B each illustrate an example of the relationship between the circumferential velocity and the phase of a rotating member (machining section).
Figure 2B:
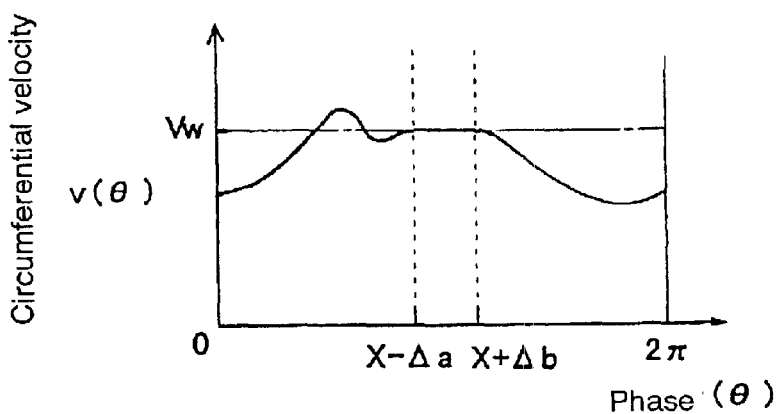
Figure 2C:
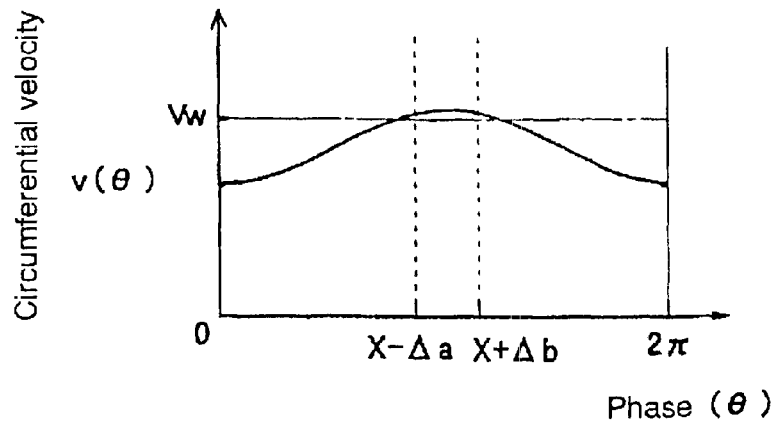

When producing an article of size L with the rotating member 2 for size M, the circumferential velocity v(θ) of the machining section 1 is set to a velocity approximate to the flow velocity $V_w$ in the working area α, while the average circumferential velocity of the machining section 1 is set to be a value smaller than the flow velocity $V_w$ in the non-working area β, as illustrated in FIG. 2A. However, depending on the control method, the circumferential velocity v(θ) of the machining section 1 may temporarily exceed the flow velocity $V_w$ of the continuous mat in the non-working area β, as illustrated in FIG. 2B. Moreover, where a radius r denotes the distance from the center of rotation of the rotating member 2 to the tip of the machining section 1, i.e., where the radius r denotes the rotational radius of the machining section 1, Expression (1) below can be derived:

$$\int_0^{2\pi} \frac{r \cdot d\theta}{v(\theta)} = T_L \quad (1)$$

where $v(\theta) \approx V_w$ or $v(\theta) > V_w$ for $x-\Delta a \leq \theta \leq x+\Delta b$, $T_L$: Amount of time required for one revolution r: Rotational radius of machining section Thus, the circumferential velocity of the rotating member 2 may change in any manner in the non-working area as long as the amount of time $T_L$ required for one revolution is constant. Moreover, in the working area α, the circumferential velocity v(θ) of the machining section 1 may be the flow velocity $V_w$ multiplied by a constant (1 or more). For example, the circumferential velocity v(θ) of the machining section 1 may slightly change in the working area α as illustrated in FIG. 2C. Note that the distance from the center of rotation of the rotating member 2 to the tip of the machining section 1 may be considered to be the radius of the rotating member 2 if there is only a small difference between the distance and the radius of the rotating member 2.

Figure 3A:
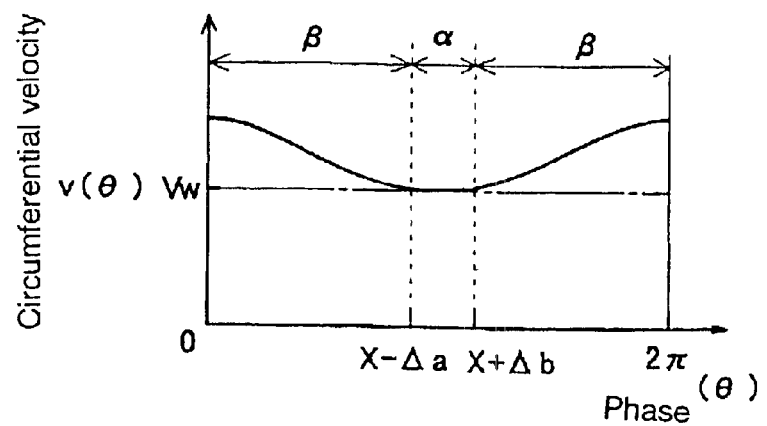
Figure 3B:
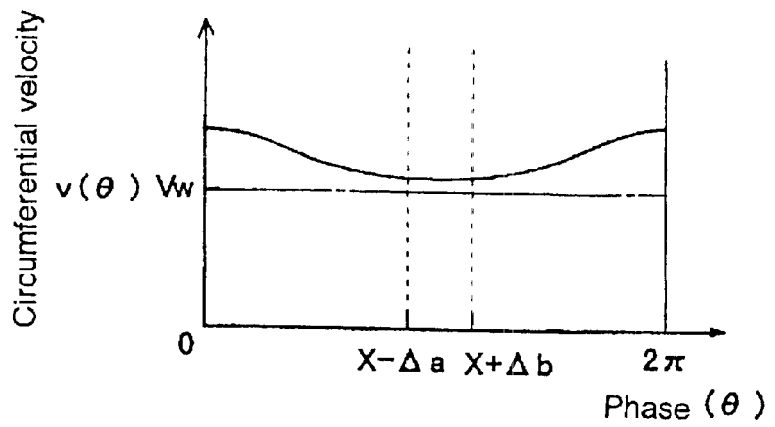

On the other hand, when producing an article of size S with the rotating member 2 for size M, the circumferential velocity v(θ) is set to a velocity approximate to the flow velocity $V_w$ in the working area α, while the average circumferential velocity is set to be a value larger than the flow velocity $V_w$ in the non-working area β, as illustrated in FIG. 3A. Thus, the circumferential velocity of the rotating member 2 may change in any manner in the non-working area as long as the amount of time $T_s$ required for one revolution, which is shown in Expression (2) below is constant.

$$\int_0^{2\pi} \frac{r \cdot d\theta}{v(\theta)} = T_S \quad (2)$$

where $v(\theta) \approx V_w$ or $v(\theta) > V_w$ for $x-\Delta a \leq \theta \leq x+\Delta b$, $T_s$: Amount of time required for one revolution r: Rotational radius of machining section While the circumferential velocity v(θ) may be the flow velocity $V_w$ multiplied by a constant (1 or more) in the working area α, the circumferential velocity v(θ) may change slightly in the working area a as illustrated in FIG. 3B, for example.

Note that when performing a size-M machining process with a roll for size M, the circumferential velocity v(θ) may be a constant value that is larger than the flow velocity $V_w$, and $T_s < T_M < T_L$ holds where $T_M$ denotes the amount of time required for one revolution.

Figure 1B:
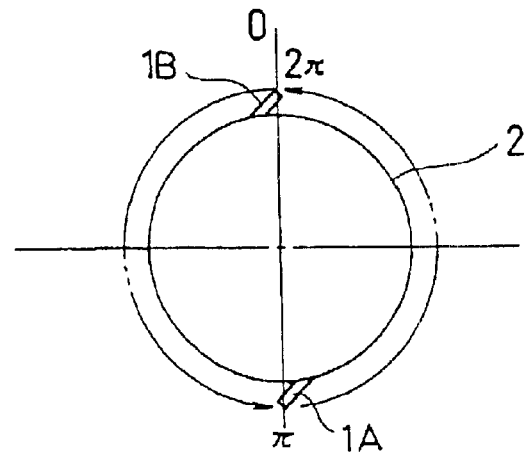
FIG. 1B illustrates an example of a rotating member provided with a plurality of machining sections.

In the present invention, a single rotating member 2 may be provided with a plurality of machining sections 1a and 1a, as illustrated in FIG. 1B.

Figure 4A:
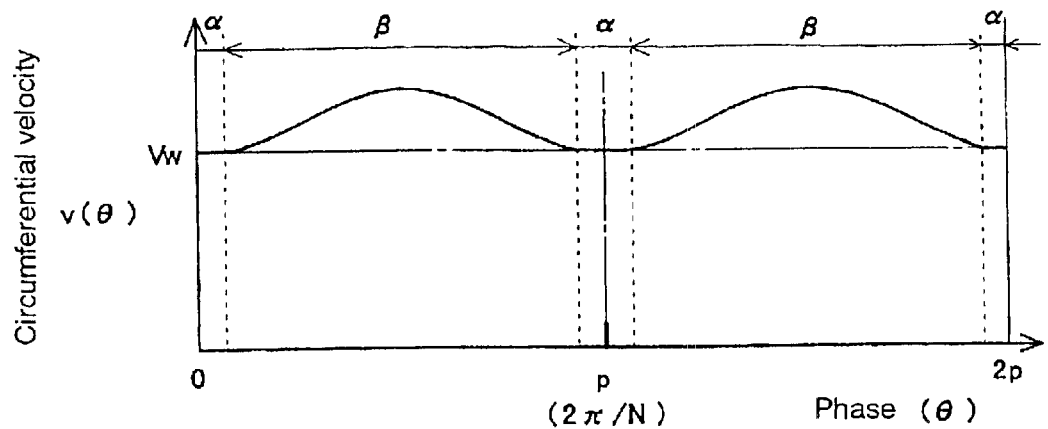
FIG. 4A illustrates the relationship between the circumferential velocity and the phase of a rotating member (machining section) in a case where the rotating member is provided with N machining sections.

In such a case, the production process can be carried out appropriately as long as the cycle time $T_i$, which is defined as the amount of time for one cycle from the machining process by the machining section 1a to the next machining process by the machining section 1b, is generally constant for each size, as shown in Expression (3) below.

$$\int_0^p \frac{r \cdot d\theta}{v(\theta)} = T_i \quad (3)$$

where p=2π/N,
- p: Rotational angel per cycle
- N: Number of machining sections provided for single rotating member,
- $T_1$: Amount of time required for one cycle for each size,
- r: Rotational radius of machining section In this case, a plurality of cycles are performed for each revolution of the rotating member, as illustrated in FIG. 4, and an angle obtained by dividing 2π by N (the number of machining sections) corresponds to one cycle. Thus, the amount of time from the machining process by the (first) machining section 1A until the next machining process (by the second machining section 1B) is defined as one cycle. In this way, articles of different sizes can be produced by controlling the production process by changing the circumferential velocity of the machining sections 1A and 1B according to the size of the article (i.e., by changing the circumferential velocity of the machining section along a predetermined velocity curve according to the size). Thus, the rotation of the rotating member is controlled so that the machining section has a predetermined circumferential velocity for the phase thereof by changing the circumferential velocity of the machining section according to the change in the phase of the machining section.

Note that in a case where the rotating member 2 is rotated in one direction, it is unlikely that the rotating member 2 is stopped (v(θ) being brought to zero) during its operation. Nevertheless, if v(θ)=0 occurs, the amount of time required for one cycle may be obtained by adding the rotating member hold time ΔT to $T_1$ as defined above. Alternatively, Expressions (1) to (3) may be applied except for the period during which v(θ)=0.

Moreover, the flow velocity $V_w$ of the web W fluctuates in some cases. Then, the rotational velocity of the rotating member 2 in one cycle may be changed so as to absorb the fluctuation in the flow velocity $V_w$. In such a case, a detector for detecting the velocity of the web W may be provided so as to control the circumferential velocity v(θ) of the machining section in proportion to the detected web velocity $V_w$.

Figure 4B:
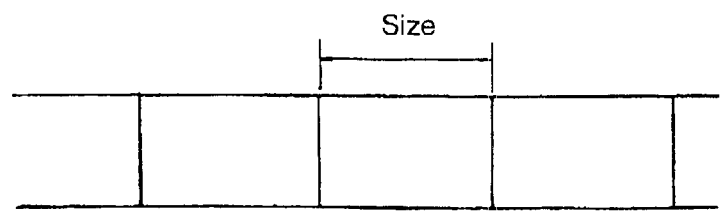
FIG. 4B and FIG. 4C are diagrams each illustrating an example of the size of a semi-finished product.
Figure 4C:
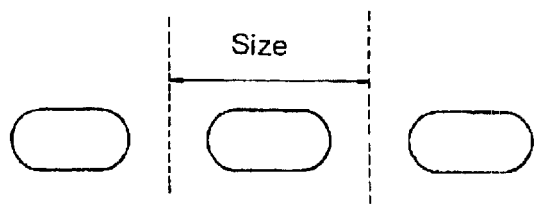

In a case where semi-finished products of an article are provided in the form of a continuous member, the size of each semi-finished product may be determined as the length of the semi-finished product in the flow direction (FIG. 4B). In a case where semi-finished products of the article are arranged separately, the size of each semi-finished product may be determined as the distance between boundaries between adjacent articles (FIG. 4C).

Note that a mat cutter unit, a seal unit, a trim cutter unit, etc., may include a rotating member having the machining section 1 and a roll opposing the rotating member, in which case the opposing roll may rotate at generally the same velocity as a semi-finished product, and the circumferential velocity v(θ) of the machining section 1 may be in synchronism with the circumferential velocity of the opposing roll in the working area. Moreover, in a case where the circumferential velocity v(θ) of the machining section 1 changes in the non-working area β, the circumferential velocity v(θ) has one or more point of inflection or extremum.

For example, such a production apparatus may be an article production apparatus including a storage section for storing the relationship between each phase of the machining section and the corresponding circumferential velocity of the machining section for each size of article, and a controller for reading out the relationship for a specified size upon specifying the size so as to control the rotation of the roll according to the size.

A method for producing articles of a plurality of sizes may include the steps of: making an absorbent; introducing an elastic member onto a web while a guide section moves the elastic member in the width direction of the web according to the shape of a leg hole for each size of article; placing the absorbent on the web; opening a hole to be the leg hole in the web according to the shape of the leg hole of the article; and cutting the web with the hole having been opened therein and the absorbent having been placed thereon according to the size of the article. The relationship of the moving velocity in the width direction of the guide and/or cutter with respect to the position in the width direction thereof may be stored for each size of article. In such a case, when a size is specified, the guide and/or the cutter may be operated at the moving velocity according to the specified size.

When a size is specified, the elastic member is placed on the web while being moved by the guide section in the width direction of the web at a moving velocity according to the specified size, or a hole is made in the web while the cutter moves in the width direction at a moving velocity according to the specified size, whereby it is not necessary to replace a unit when the size is changed to another.

Moreover, even for articles of the same size, the size of the articles may vary in some cases according to an expansion/contraction of a member or a semi-finished product. In such a case, the position at which the member or the semi-finished product is machined can be adjusted according to the expansion/contraction of the member or the semi-finished product based on the principle described above.

Embodiments of the present invention will now be described with reference to the drawings.

First Embodiment

Figure 5:
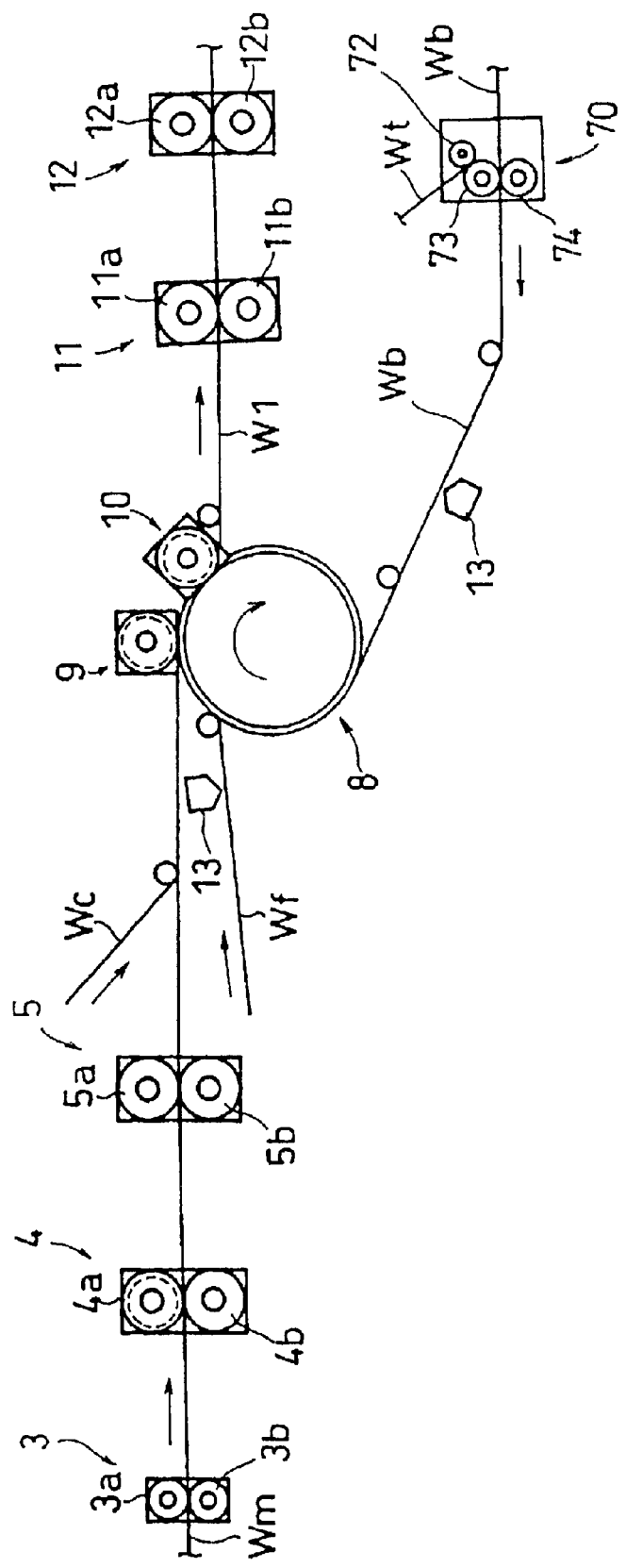
FIG. 5 illustrates an example of a production line for producing an article.

FIG. 5 is a diagram illustrating an example of a production apparatus for producing an article. Specifically, the production apparatus is capable of producing a diaper, which is a type of worn article. The production apparatus includes at least one rotating member having a machining section.

A press unit 3 includes a press roll 3a and an anvil roll 3b. The press unit 3 illustrated in FIG. 5 presses a continuous mat Wm, and thus does not normally have a protrusion. However, in a case where a particular position of the continuous mat Wm is pressed or where the position at which it is pressed changes according to the size, the press roll 3a acting as a rotating member may be controlled based on the principle of the present invention. The mat Wm capable of absorbing a liquid that is passed to the press unit 3 is formed to a predetermined thickness by the press roll 3a. Note that it is preferred that the circumferential velocity of the anvil roll 3b is generally the same as the flow velocity of the mat Wm.

An embossing unit 4 includes an embossing roll 4a and a counter roll 4b, the embossing roll 4a being capable of applying one or both of a pressure and a heat to a member, etc. A plurality of pins are provided on the surface of the embossing roll 4a, and the embossing unit 4 makes dents in the mat Wm, which has been pressed to a predetermined thickness. Note that with the dents, effects such as an increase in the strength of the mat Wm and an improvement in the absorptivity can be expected. While surface of the counter roll 4b may be a smooth curved surface, the counter roll 4b may be provided with holes corresponding to the pins of the embossing roll 4a. The embossing unit 4 illustrated in FIG. 5 includes pins that are arranged uniformly across the entire surface of the embossing unit 4 so as to emboss the continuous mat Wm. Note that the embossing unit 4 is not limited to those that perform a pin-embossing process. For example, the surface of the embossing roll 4a may be provided with a single line blade, a protrusion having a mesh shape or a lattice shape, or protrusions having a heart shape, a clover shape, a diamond shape, a spade shape, a circular shape, a crescent shape, or the like.

In a case where a particular position of the mat Wm is embossed, and the position at which embossing is performed changes depending on the size, the embossing roll 4a acting as a rotating member may be controlled based on the principle of the present invention. Note that in a case where the counter roll 4b is provided with holes corresponding to the pins, the counter roll 4b rotates according to the rotation of the embossing roll 4a.

A cutter unit 5 includes a cutter roll 5a and an anvil roll 5b. The cutter unit 5 cuts the embossed mat Wm into pieces of a predetermined length. The predetermined length is dependent on the size of the article. The cutter roll 5a acting as a rotating member is controlled based on the principle of the present invention. Note that in a case where the mat Wm is not continuous but is formed in separate pieces, the cutter unit 5 is not needed.

A cuff member Wc is introduced onto the mat Wm, which has been cut into pieces of a predetermined length. The cuff member Wc may be fixed to the mat Wm with an adhesive or a seal. While the adhesive is applied on at least one of the cuff member Wc and the mat Wm, the application may be either continuous or intermittent. In a case where a hot melt is used as the adhesive, the application may be a bead application, a coater application, a spray head application, a curtain application, a spray application, a transfer roll application, etc. The hot melt may be a synthetic rubber-based hot melt, an olefin-based hot melt, etc. The mat Wm having undergone a predetermined machining process is passed to an assembly drum 8. Moreover, the cuff member Wc may be provided on the backsheet Wb.

Moreover, a frontal tape Wt is attached by a tape attachment unit 70 to a backsheet Wb on which the mat Wm is to be layered.

Figure 6A:
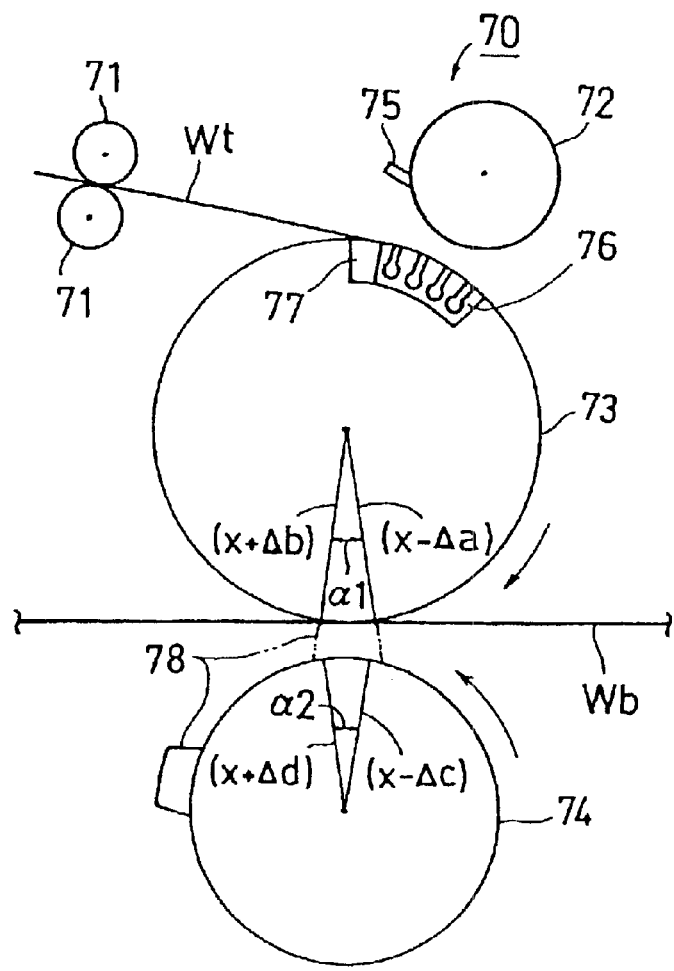
FIG. 6A illustrates an example of a tape attachment unit 70.

FIG. 6A is a diagram illustrating an example of the tape attachment unit 70. The tape attachment unit 70 includes a pair of pinch rolls 71 and 71 capable of pushing out a predetermined length of the frontal tape Wt, a cutter roll 72 having at least one blade for cutting the tape Wt, a transfer roll 73 for transferring the cut tape Wt, and a press roll 74 for pressing together the tape Wt and the backsheet Wb.

For example, the pinch rolls 71 and 71 may push out the tape Wt either continuously or intermittently. Since the transfer roll 73 rotates while a sucking portion 76 thereof sucks the tape Wt, the transfer roll 73 and the tape Wt are rubbed against each other. Specifically, in a case where the tape Wt is pushed out continuously, the circumferential velocity of the transfer roll 73 is greater than the velocity at which the tape Wt is fed by the pinch rolls 71 and 71. Moreover, even in a case where the tape Wt is pushed out intermittently, the circumferential velocity of the transfer roll 73 is greater than the velocity at which the tape Wt is fed by the pinch rolls 71 and 71 in terms of the average velocity. The tape Wt is cut into a predetermined length by being sandwiched between at least one blade 75 of the cutter roll 72 and a table 77 of the transfer roll 73. The table 77 does not have a suction hole as the sucking portion 76 since it receives the blade 75. Moreover, the length of the sucking portion 76 in the rotation direction is greater than the predetermined length of the tape Wt. Moreover, when the blade 75 and the table 77 abut against each other via the tape Wt, the circumferential velocity of the blade tip of the blade 75 may be substantially equal to, or greater than, that of the transfer roll 73.

Normally, the cutter roll 72 rotates while maintaining a predetermined circumferential velocity. However, as illustrated in the description of the principle of the present invention, the circumferential velocity of the cutter roll 72 may be changed during one cycle. In this case, one cycle is defined as a period of time from the cutting off of a piece of the tape Wt to the cutting off of the next piece of the tape Wt. Therefore, the cycle also varies depending on other factors such as the number of blades 75 provided on the cutter roll 72.

The transfer roll 73 transfers the cut tape Wt to a working area (x−Δa to x+Δb) while a protrusion 78 of the press roll 74 moves to a working area (x−Δc to x+Δd), and the tape Wt is fixed to the backsheet Wb by the transfer roll 73 and the press roll 74 in an overlap area where these working areas overlap. Specifically, the press roll 74 includes at least one protrusion 78, and the protrusion 78 presses the backsheet Wb and the tape Wt onto the transfer roll 73 so as to adhere the tape Wt to the backsheet Wb. The tape Wt may include an adhesive area in order to adhere the tape Wt to the backsheet Wb. Alternatively, an adhesive may be applied on the tape Wt during a period from the feeding of the tape Wt from the pinch rolls 71 and 71 until the cutting off thereof by the cutter roll 72. Alternatively, an adhesive may be applied before the tape Wt is fed from the pinch rolls 71 and 71 in a case where the surface of at least one pinch roll 71 is coated with a material (e.g., silicon, Teflon (R), etc.) having a high peelability to the adhesive.

If the size is not changed, the circumferential velocity of the transfer roll 73 and the circumferential velocity of the protrusion 78 of the press roll 74 are generally the same as the velocity of the backsheet Wb. However, even in a case where the size of article is changed and the interval at which the tape Wt is attached to the backsheet Wb is changed, the transfer roll 73, etc., may be controlled based on the principle of the present invention so that the circumferential velocity of the transfer roll 73, etc., in each working area is generally the same as the velocity of the backsheet Wb. The press roll 74 may also be controlled so that the circumferential velocity of the protrusion 78 is generally the same as the velocity of the backsheet Wb in the working area (x−Δc to x+Δd). Thus, the transfer roll 73 may be controlled so that the circumferential velocity of the sucking portion 76 holding the tape Wt is generally the same as the velocity of the backsheet Wb in the working area (x−Δa to x+Δb) of the transfer roll 73. Moreover, the times at which the sucking portion 76 and the protrusion 78 enter the respective working areas are controlled so that the tape Wt can be pressed against the backsheet Wb in an area where the working areas overlap.

As illustrated in FIG. 5, in the assembly drum 8, the backsheet Wb, onto which an elastic member Wf has been introduced, and the mat Wm, onto which the cuff member Wc has been introduced, are laid on each other, and the mat, etc., is sealed by a seal unit 9 for sealing the vicinity of the interface between adjacent articles and a seal unit 10 for sealing the sides of the articles, thereby producing a combined member W1. The method for introducing the elastic member Wf will be described later.

Figure 6B:
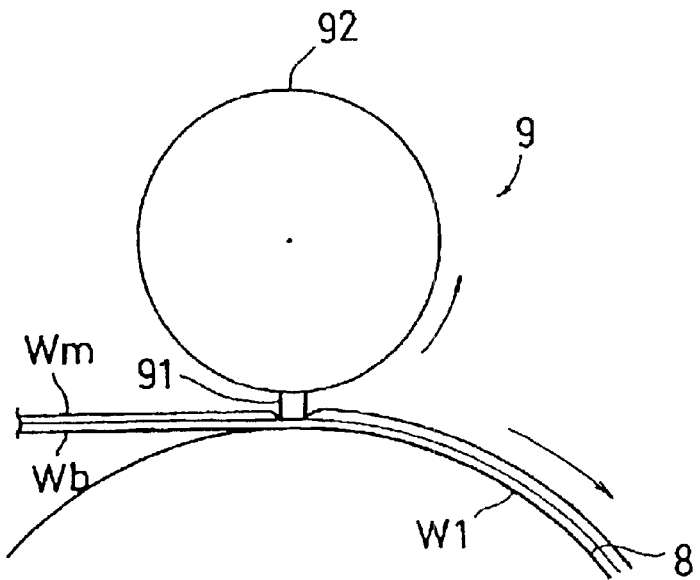
FIG. 6B illustrates an example of a seal unit 9.

FIG. 6B is a diagram illustrating an example of the seal unit 9. A seal roll 92 includes at least one protrusion 91, and seals semi-finished products between the protrusion 91 and the assembly drum 8, e.g., the mat Wm and the backsheet Wb. The seal may be a heat seal, an ultrasonic seal, or the like. Moreover, in a case where an amount of heat for sealing the member cannot be given at once, the sealing may be performed in a plurality of steps. Moreover, a preliminary heating process may be performed on a portion to be sealed before the sealing process. In a case where the sealing may be performed in a plurality of steps, the seal unit 9 is provided for each of a plurality of assembly drums 8. Moreover, the preliminary heating process may be performed by using a heater arranged on the assembly drum 8, a hot air discharged toward the member to be sealed, or a combination thereof.

Figure 1C:
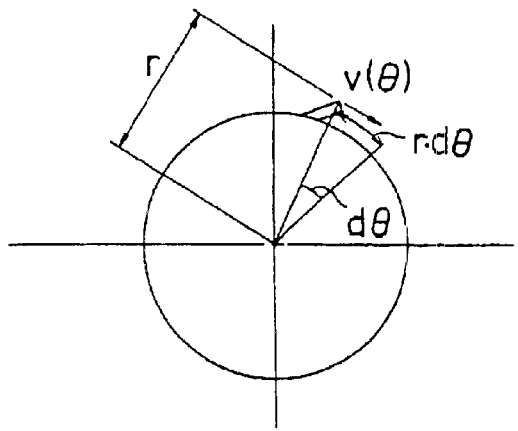
FIG. 1C illustrates an example of the relationship between the circumferential velocity and the rotational velocity.

When a heat seal process is performed, the protrusion 91 of the seal roll 92 applies at least a pressure and a heat to a portion of the mat and/or the backsheet to be adhered (heat-sealed) in order to adhere the mat and the backsheet to produce the combined member W1. The configuration of the seal roll 92 is substantially the same as that of the rotating member 2 illustrated in FIG. 1 with the machining section 1 thereof being replaced with a seal blade. Thus, it is possible to produce an article of a given size by rotating the seal roll 92 at a constant circumferential velocity. Moreover, it is possible to produce articles of other sizes based on the principle of the present invention without replacing the seal roll 92.

As illustrated in FIG. 5, in order to open a leg hole in the combined member W1, the combined member W1 is passed to a trim cutter unit 11 so as to cut off a portion corresponding to the leg hole.

Figure 7:
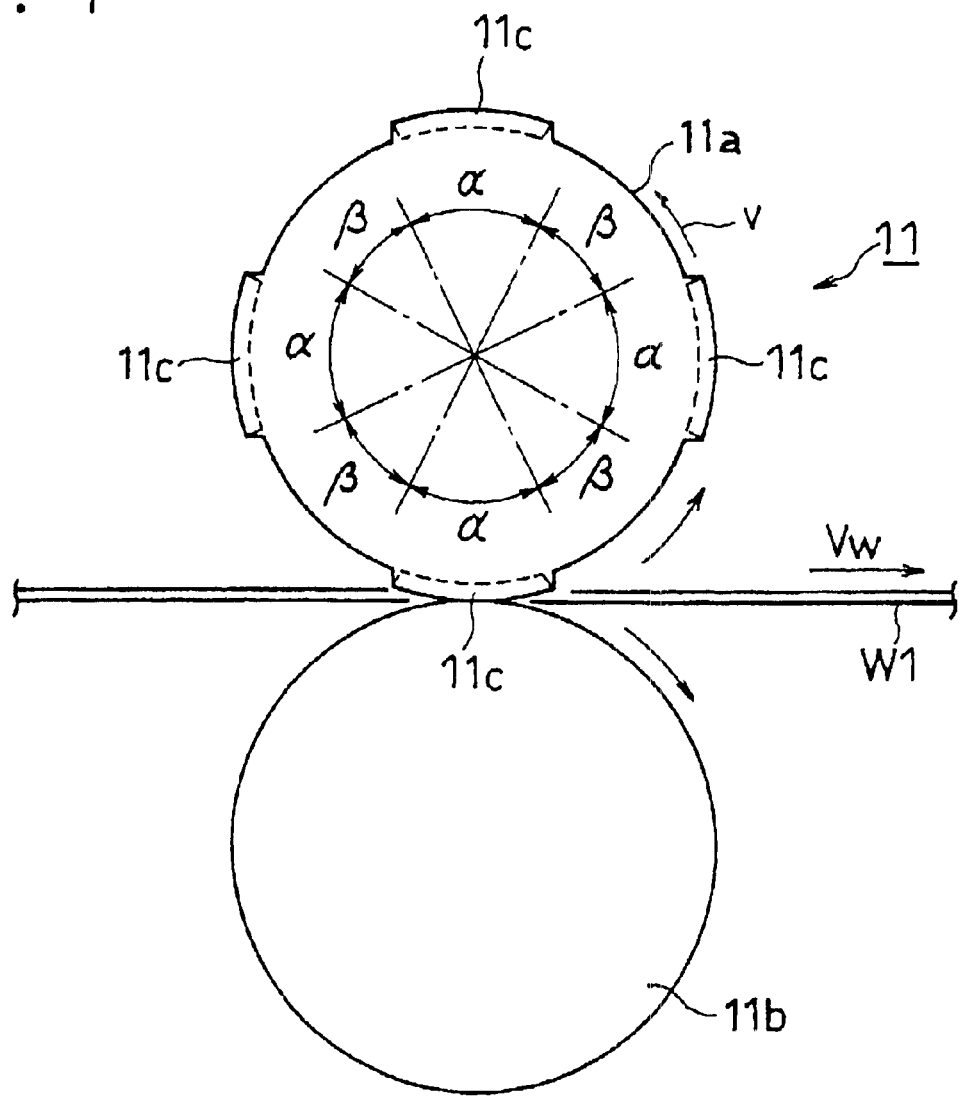
FIG. 7 illustrates an example of a trim cutter unit.

FIG. 7 illustrates an example of the trim cutter unit 11.

The trim cutter unit 11 includes a trim roll 11a on which at least one loop-shaped blade 11c is arranged, and an anvil roll 11b. A member between the blade 11c and the anvil roll 11b is cut off.

Next, a method for controlling the trim roll 11a will be described.

In a case where a worn article having a leg hole of size M is produced by using the trim roll 11a for forming a leg hole of size L, the trim roll 11a is rotated so that the circumferential velocity $v(\theta)$ of the trim roll 11a is greater than the flow velocity $V_w$ of the combined member W1 by a predetermined proportion R1 in the working area $\alpha$ of the trim roll 11a. In this way, the distance by which the blade 11c contacts the combined member W1 is shorter than that when producing a leg hole of size L. Thus, a leg hole having a smaller area than a leg hole of size L can be opened in the combined member W1. In a case where a worn article having a leg hole of size S by using the trim roll 11a for a leg hole of size L, the trim roll 11a can be similarly rotated so that the circumferential velocity $v(\theta)$ of the trim roll 11a is greater than the flow velocity of the combined member W1 by a predetermined proportion R2 in the working area $\alpha$ of the trim roll 11a. Herein, R1<R2.

As illustrated in FIG. 5, the combined member W1 is finally divided into pieces by a final cut unit 12. With the final cut unit 12, as with the cutter unit 5, it is possible to produce an article of a given size by rotating a cutter roll 122 at a constant circumferential velocity, and it is possible to produce articles of other sizes based on the principle of the present invention without replacing the cutter roll 122.

Note that the production apparatus illustrated in FIG. 5 includes an adhesive supplier 13. In a case where a hot melt is used as an adhesive, the application may be performed in any of the forms of application described above. Moreover, the interval at which the adhesive supplier 13 applies an adhesive may be changed according to the size of the article.

Moreover, the timing at which an adhesive is applied may be in synchronism with a velocity signal, an interval signal or a timing signal CAT or CCT to be described later.

An example of a control system for controlling the rotating member will now be described.

Figure 8A:
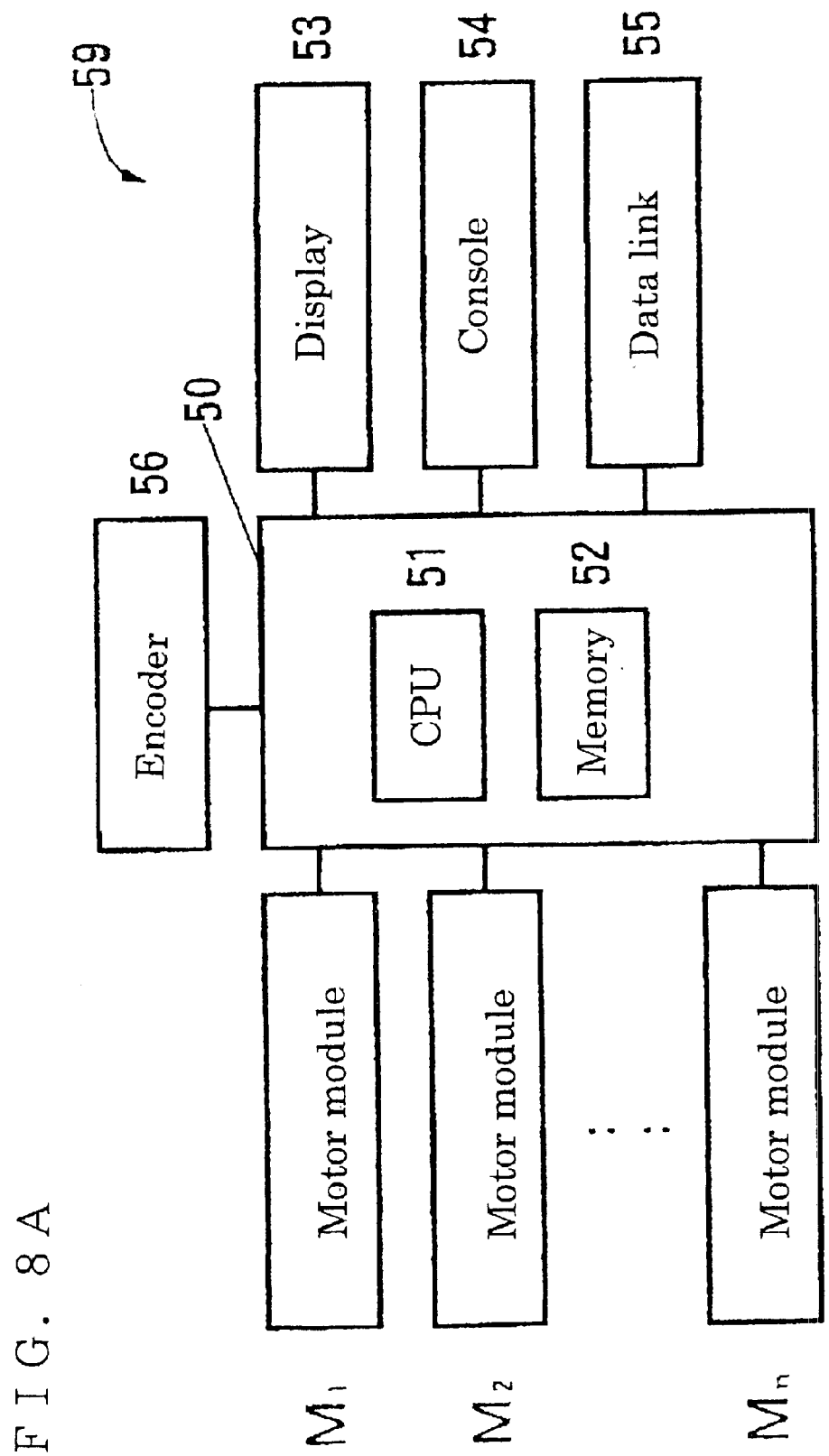
FIG. 8A and FIG. 8B each illustrate an example of a control system.

A control system 59 illustrated in FIG. 8A includes motor modules $M_1$ to $M_n$ and a controller 50 having a CPU (central processing unit) 51 and a memory 52, and may further include a display 53, a console 54, a data link 55 and an encoder 56. As illustrated in FIG. 8C, the motor module M includes a servo motor 61 for rotating the rotating member, and an amplifier 62 for amplifying a rotation signal applied to the servo motor 61. Herein, the term "amplification" is not limited to an analog amplification, but in a case where the rotation signal is a digital signal, for example, it may also include a conversion into a signal with which the servo motor can be rotated based on the value represented by the digital signal.

For example, relationship information indicating the relationship between the circumferential velocity of the rotating member and the phase of the rotating member illustrated in FIG. 2A to FIG. 2C is stored in memory 52. The relationship information may either be in the form of data or be given by Expressions (1) to (3) above, or the like. It is preferred that the relationship information is provided in the form of data in order to reduce the number of calculations for the CPU 51, etc. For example, a phase of the rotating member and a corresponding circumferential velocity of the rotating member may be stored as a pair of data. Alternatively, the relationship information may be stored while being associated with the size of article in the memory 52, etc. For example, the relationship information and the size of article may be stored in the form of a table, wherein the phase of the rotating member is associated with the column of the table, the size of article is associated with the row of the table, and a circumferential velocity of the rotating member corresponding to each phase of the rotating member and each size of article is written in the table.

Moreover, when the relationship information is stored in the memory 52, etc., it may be input by an operator through the console 54, or a small portable terminal such as a notebook personal computer may be linked with the data link 55 and the relationship may be transferred from the small portable terminal to the memory 52. Note that in a case where the relationship information and the size of article are stored while being associated with each other, the relationship information corresponding to a size of article may be read out from the memory 52 by the operator operating the console 54, and the CPU 51 may control the servo motor 61 according to the expression or data so as to control the rotation of the rotating member.

Moreover, it is possible to realize a two-way communication with external computers outside the production apparatus by linking the data link 55 to the Internet. In this way, the production apparatus can easily receive an updated version of the relationship information via the Internet. Moreover, the production apparatus may be directly controlled by an external computer obtaining information of an encoder and a sensor S to be described later via the Internet.

The encoder 56 sends velocity information regarding the line velocity of the production line as illustrated in FIG. 5 to the CPU 51. The encoder 56 may be provided in any place as long as the production line velocity information can be obtained. For example, the encoder 56 may detect information regarding the rotation of at least one of the mat cutter unit 5, the final cut unit 12 and the assembly drum 8 so as to produce velocity information. Some or all of the servo motors 61 are rotated in synchronism with the velocity information from the encoder 56. In other words, the phase of the rotating member at the reference position is synchronized by the velocity information. The CPU 51 produces a rotation signal for the servo motor 61 based on the relationship information and the velocity information, and sends a rotation signal to each of the motor modules $M_1$ to $M_n$. In the motor module M, the rotation signal is amplified by the amplifier 62, and the servo motor 61 is rotated based on the amplified signal. Such a configuration imposes a substantial load on the CPU 51 of the controller 50, and therefore may be applied to a production line that is operated at a relatively low speed.

The control system 59 may include a motor module L as illustrated in FIG. 8D instead of the motor module M. The motor module L may include the servo motor 61 for rotating the rotating member, the amplifier 62 for amplifying a rotation signal to be applied to the servo motor 61, a memory 63 capable of storing relationship information between the circumferential velocity of the rotating member and the phase of the rotating member, and a CPU 64 for producing a rotation signal. The motor module L may include the data link as described above.

The relationship information of the controller 50 is sent to, and stored in, the memory 63 of the motor module L. Moreover, the controller 50 sends velocity information from the encoder 56 to the motor module L. The motor module L produces a rotation signal based on the velocity information and the relationship information sent thereto. The amplifier 62 amplifies the rotation signal, and the servo motor 61 is rotated based on the amplified signal. Note that in a case where the relationship information and the size of article are stored while being associated with each other, the operator may operate the console 54 to specify a size of article, whereby the relationship information corresponding to the size of article is read out from the memory 52 and sent to the memory 63. Alternatively, the relationship information stored in the memory 63 may be selected by the operator.

Figure 8B:
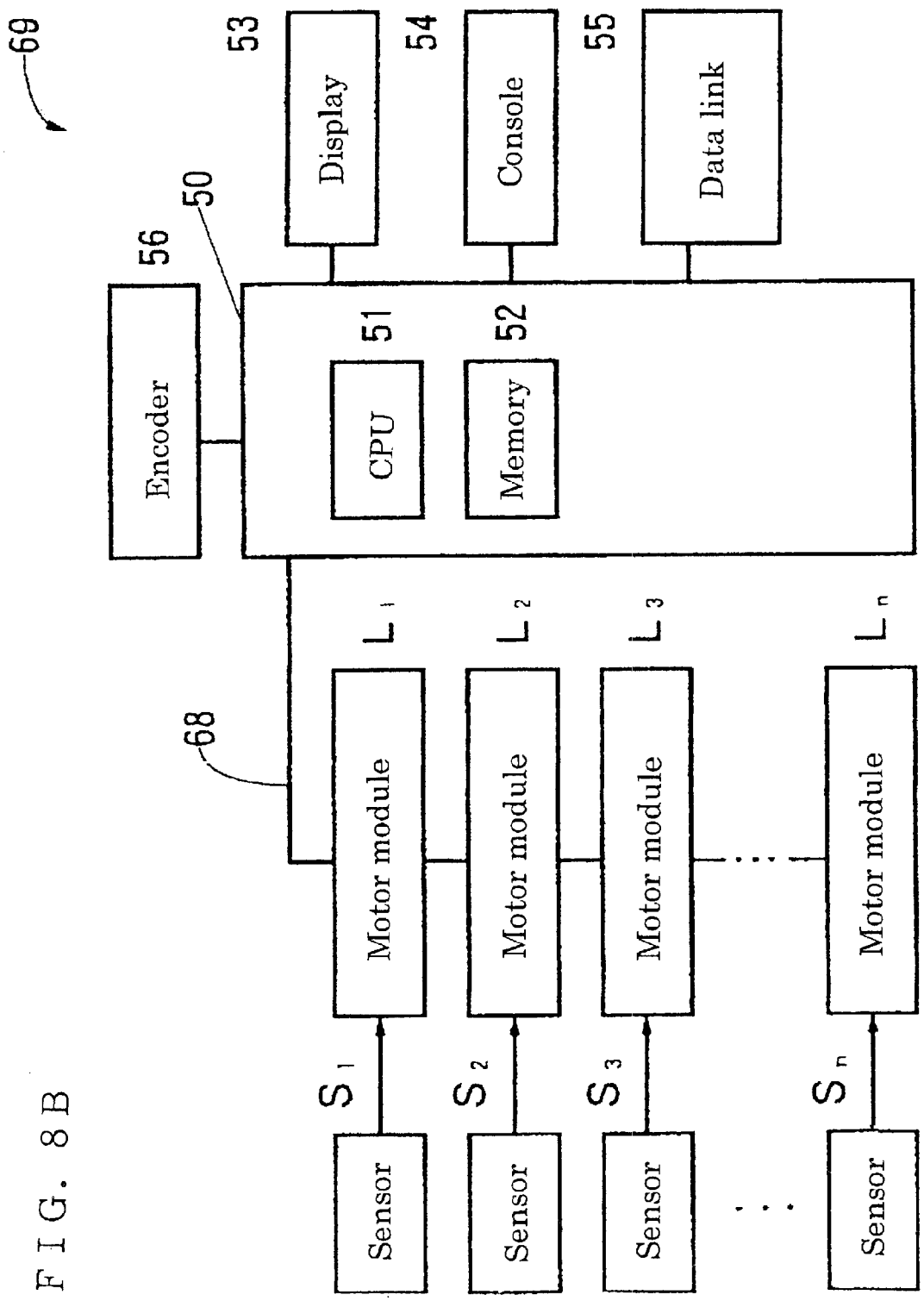
Figure 13:
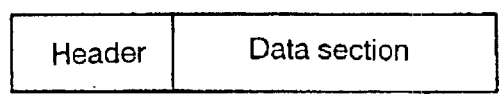
FIG. 13 illustrates an example of information output from a controller.

The control system for controlling the rotating member may be a control system 69 illustrated in FIG. 8B. With the control system 69, the number of interconnections can be reduced as compared with the control system 59. Therefore, information output from the controller 50 of the control system 69 may include a header section and a data section as illustrated in FIG. 13. One or both of a control instruction and address information is written in the header section.

Herein, a control instruction may be, for example, an instruction to write information of the data section to the memory 63, or an instruction to erase data stored in the memory 63. Moreover, in a case where there are a plurality of motor modules L, the address information indicates which motor module L is to receive one or both of the control instruction and the information of the data section. One or both of the relationship information and the velocity information may be written in the data section. Note however that since the velocity information is important information for synchronizing a rotating member with another rotating member, the controller 50 may send the velocity information independently to an interconnection 68 (the term "interconnection" refers not only to a wire or a coaxial cable, but may also include an optical fiber, etc., and may even be a wireless connection as long as data, etc., can be communicated therethrough) while shifting the phases of the header section and the data section illustrated in FIG. 13. Alternatively, the velocity information may be sent to the motor module L while using different frequencies for the header section and for the data section. Moreover, those described above may be used in combination, and the velocity information may include a code for error correction.

An example of a control method in a case where the sensor S is connected to the motor module L of the control system 59 or 69 will now be described.

Figure 14:
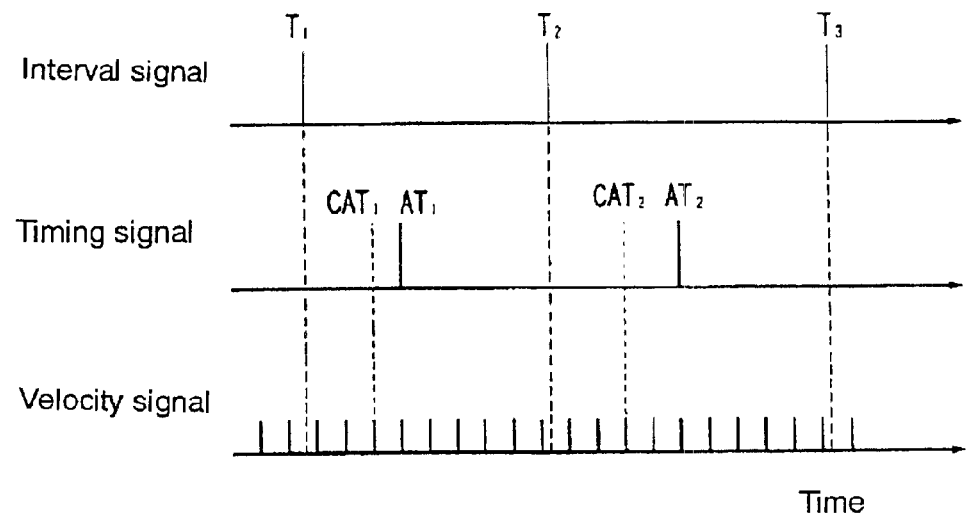
FIG. 14 and FIG. 15 each illustrate an example of the relationship between an interval signal, a timing signal and a velocity signal on a time axis.

The flow velocity of a semi-finished product basically coincides with the velocity information obtained from the encoder 56. Assuming that the velocity information is represented by a velocity signal that is composed of pulses each of which is output when the semi-finished product is moved by a predetermined distance, the CPU 51 (or 64) generates a timing signal $AT_1$, $AT_2$ each time a predetermined number of velocity signals are outputs, as illustrated in FIG. 14, and the rotation signal is produced based on the relationship information and the timing signal $AT_1$, $AT_2$. For example, the CPU 51 (or 64) controls the machining section so that the machining section reaches the working area at a predetermined circumferential velocity according to the timing signal $AT_1$, $AT_2$.

However, where the semi-finished product expands or contracts, the flow velocity of the semi-finished product does not locally coincide with the velocity information in some cases. In order to accommodate such a local shift, the phase and the velocity of the rotating member may be controlled based on information regarding the expansion/contraction of the semi-finished product. An example of a method for controlling the rotating member while correcting a lag or a lead of such a semi-finished product will be described.

This method corrects a lag or a lead of the machining section by generating a timing signal when a predetermined number of velocity signals have been issued from an interval signal produced by the sensor S or after passage of a predetermined amount of time from the interval signal.

The sensor S is capable of detecting a reference point of the semi-finished product that is marked on the semi-finished product. Reference points may be marked in advance at regular intervals on the semi-finished product, the edge of a cut-off semi-finished product or an attached member, e.g., a tape, may be used as a reference point, or a reference point may be written on a portion that is cut off during the producing process or a portion that will not finally be a part of the article. This is for ensuring that the mark will not finally be left on the article. Moreover, the mark does not have to be confirmed visually, but may alternatively be confirmed by using UV light, for example.

When a reference point is detected by the sensor S, which is arranged at a predetermined position in the production apparatus, an interval signal $T_1$, $T_2$, $T_3$ is sent to the CPU 64. The controller 50 sends the velocity signal, which is velocity information from the encoder 56, to the CPU 64. When the CPU 64 counts a predetermined number G of velocity signals after receiving the interval signal $T_1$, $T_2$, $T_3$, the CPU 64 generates a timing signal $CAT_1$, $CAT_2$. The rotation signal is produced according to the timing signal $CAT_1$, $CAT_2$ so that the machining section reaches the working area at a predetermined circumferential velocity. Note that in a case where the line velocity is constant, the timing signal $CAT_1$, $CAT_2$ may be produced after passage of a predetermined period D from the receipt of the interval signal $T_1$, $T_2$, $T_3$. Note that the CPU 64 can know the rotational velocity and the rotational position (phase) of the servo motor 61. For example, the servo motor 61 may include an encoder, the CPU 64 may monitor the rotation signal and estimate the rotational velocity and the rotational position of the servo motor 61 based on the rotation signal, or the CPU 64 may monitor an amplified signal that is applied to the servo motor 61, and may estimate the rotational velocity and the rotational position of the servo motor 61 based on the signal.

A next method corrects the timing signal $CAT_1$, $CAT_2$ based on the information regarding the expansion/contraction of the semi-finished product, and corrects the position (or timing) at which the semi-finished product is machined based on corrected timing signal $CCT_1$, $CCT_2$. The information regarding the expansion/contraction of the semi-finished product may be produced based on the interval between reference interval signals and the interval between actually-measured interval signals. For example, the information regarding the expansion/contraction of the semi-finished product may be produced based on velocity signals that are measured between interval signals and a reference value that is issued between the interval signals. Specifically, the expansion/contraction information may be obtained based on the ratio between the number of velocity signal pulses that are measured between interval signals and the reference number of velocity signal pulses that are issued between the interval signals.

Figure 15:
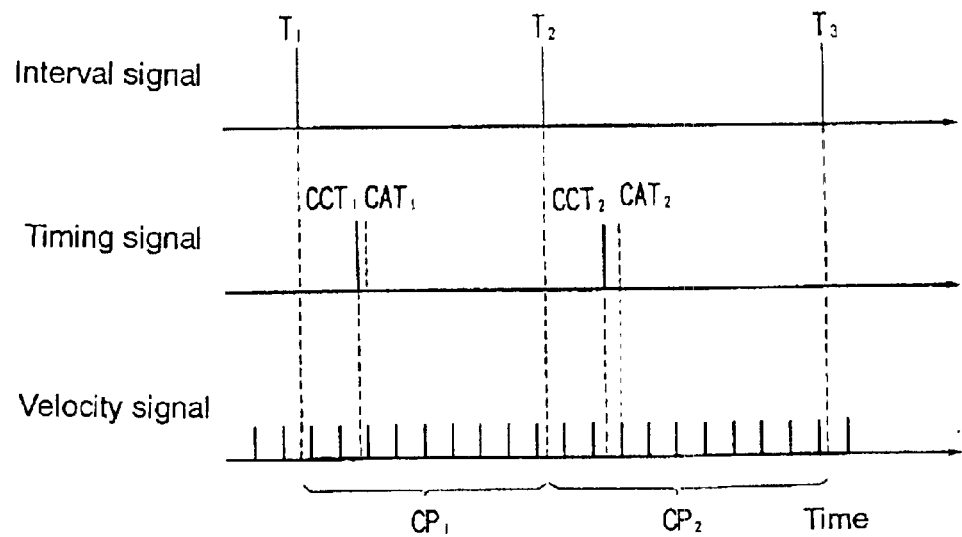

The average number (the reference pulse number) of velocity signals that are generated between interval signals is denoted as STP. The average number STP may be predetermined or may be the average value of actually-measured values. In FIG. 15, the number of velocity signals that are generated between the interval signals $T_1$ and $T_2$ is denoted as $CP_1$, and the number of velocity signals that are generated between interval signals $T_2$ and $T_3$ is denoted as $CP_2$. While the predetermined number G of velocity signals can be counted from the interval signal $T_1$, $T_2$ in the previous method, the predetermined number G is corrected based on the expansion/contraction information in the present method. For example, the timing signal $CCT_1$ is produced when a number $G \cdot CP_1/STP$ of velocity signals are counted after the interval signal $T_1$. Similarly, the timing signal $CCT_2$ is produced when a number $G \cdot CP_2/STP$ of velocity signals are counted after the interval signal $T_2$. Note that when the value $G \cdot CP_1/STP$ is not an integer, the value $G \cdot CP_1/STP$ may be rounded to the nearest whole number, rounded up or rounded down, so as to obtain an integer value. Alternatively, the time corresponding to $G \cdot CP_1/STP$ between velocity signals may be calculated by the CPU 64, and a timing signal may be produced at the time.

Similarly, the predetermined period D may be corrected based on the expansion/contraction information. For example, the timing signal $CCT_1$, $CCT_2$ may be produced after passage of a predetermined period $D \cdot CP_1/STP$ from the receipt of the interval signal $T_1$, $T_2$.

Next, when a hole is opened in the semi-finished product by the rotating member at a predetermined number of revolutions with the semi-finished product being in a contracted state, and then the semi-finished product with the hole opened therein is returned to a normal state, the hole opened in the semi-finished product is larger than a hole that is opened in a state where the semi-finished product is not contracted. Therefore, it is preferred to make a correction so that the hole has a correct size as much as possible. An example will now be described where the circumferential velocity $v(\theta)$ of the machining section in the working area is corrected based on the expansion/contraction information in a case where the semi-finished product expands or contracts in the flow direction.

In a case where the rotating member is a trim cutter and the machining section is a loop-shaped blade, the length by which the semi-finished product is cut off by the trim cutter in the flow direction is changed according to the expansion/contraction information. For example, when the number of velocity signals generated between the interval signals is smaller than the average number STP of velocity signals that are generated between the interval signals, it is assumed that the section of the semi-finished product corresponding to the interval signals is contracted. In such a case, the trim cutter is rotated at a velocity greater than the velocity $v(\theta)$ at which a hole is opened by the trim cutter in the semi-finished product in a normal state, whereby the amount of time for which the trim cutter contacts the semi-finished product is shortened, and the trim cutter can open a hole that is short in the flow direction with the semi-finished product being contracted.

Where the number of velocity signals between the interval signals is denoted as CP and the average number is denoted as STP, the circumferential velocity of the trim cutter in the working area may be $STP/CP \times v(\theta)$. This similarly applies to a case where a section corresponding to the interval signals is expanded.

In a case where for some reasons, an interval signal is not issued from the sensor S or the CPU 64, etc., does not receive an interval signal, a current interval signal may be produced based on the previous interval signals by using an estimation method such as a least square method or a maximum likelihood method. Moreover, the current interval between the previous interval signals may be used as the interval between the interval signals. Moreover, the interval signals of the sensor S may be observed by an observer. Such signal compensations may be applied to signals that are produced by a signal generation source other than the sensor S, such as an encoder, etc.

The signal from the sensor S may be transmitted to a motor module L that is not directly connected to the sensor S. This is because it is then possible to share the expansion/contraction information, etc., with other motor modules L. With such sharing of information, a motor module L can know that a section of the semi-finished product is expanded/contracted even if the sensor S is not directly connected to the motor module L. For example, if the distance between the position at which the sensor S is provided and the rotating member of the servo motor 61 of a motor module L that needs information of the sensor S is known and registered in advance in the memory 52 or 62, one or both of the phase and the circumferential velocity of the machining section of the rotating member can be corrected by using the expansion/contraction information, or the like, based on information such as the line velocity of the production line and the time at which the sensor S obtains information, even for a motor module L to which the sensor S is not directly connected.

Note that the rotating member may not be rotated directly by a servo motor, or the like. For example, a main motor may be rotated at a generally constant rotational velocity and the power may be transmitted to the rotating member via a differential device. Thus, a servo motor, or the like, may change one or both of the phase and the circumferential velocity of the rotating member via the differential device.

Figure 18:
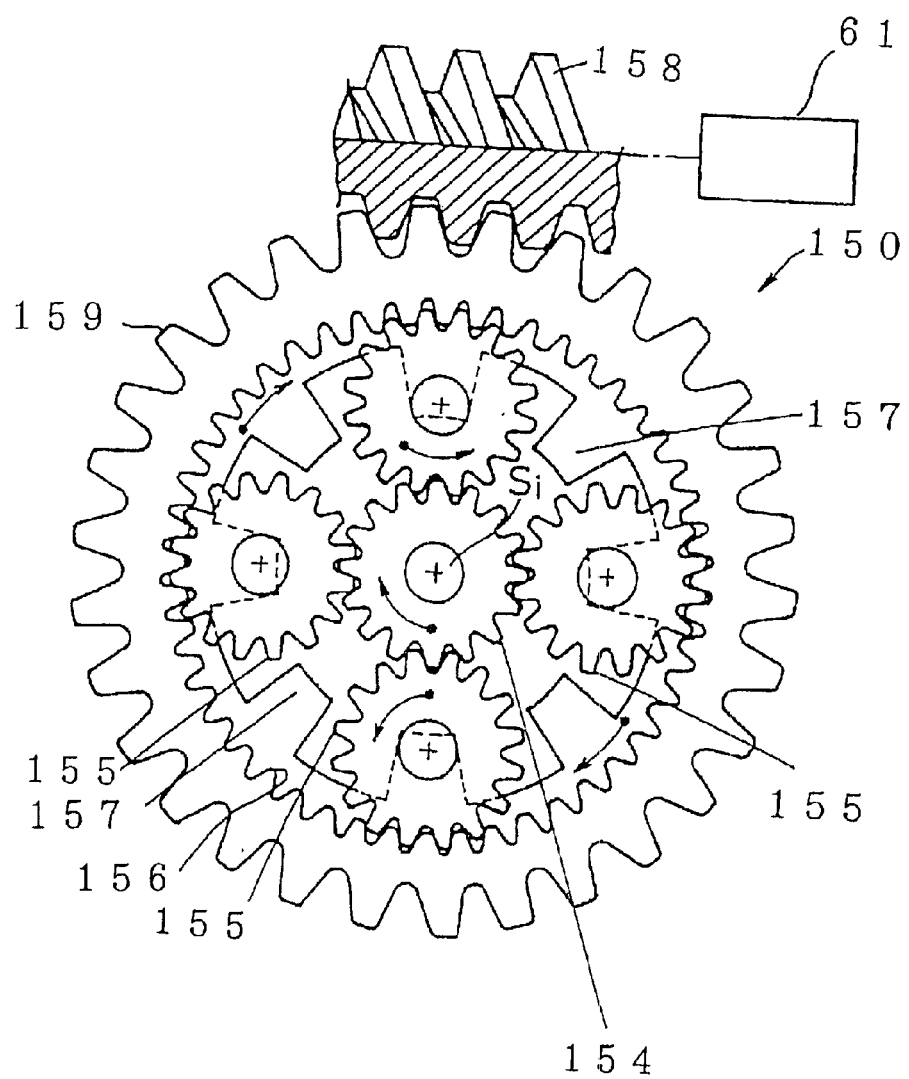
FIG. 18 illustrates an example of a planetary gear device.

An example of a differential device is a planetary gear device. FIG. 18 illustrates an example of a planetary gear device. A planetary gear device 150 includes a sun gear 154, a plurality of planetary gears 155, an internal gear 156 and a carrier 157. The sun gear 154 and the plurality of planetary gears 155 are arranged inside the internal gear 156, the plurality of planetary gears 155 and the internal gear 156 mesh with each other, and the plurality of planetary gears 155 are rotated also by the internal gear 156. The center shaft of each of the plurality of planetary gears 155 is rotatably attached to the carrier 157, and the carrier 157 rotates as the plurality of planetary gears 155 revolve around the sun gear 154. Herein, a power Si of the main motor is transmitted to the sun gear 154, and the rotating member is rotated by the rotation of the carrier 157. The circumferential velocity of the rotating member may be changed by the servo motor 61 controlling the rotation of the internal gear 156 via a worm 158 and a worm wheel 159.

Second Embodiment

Figure 9:
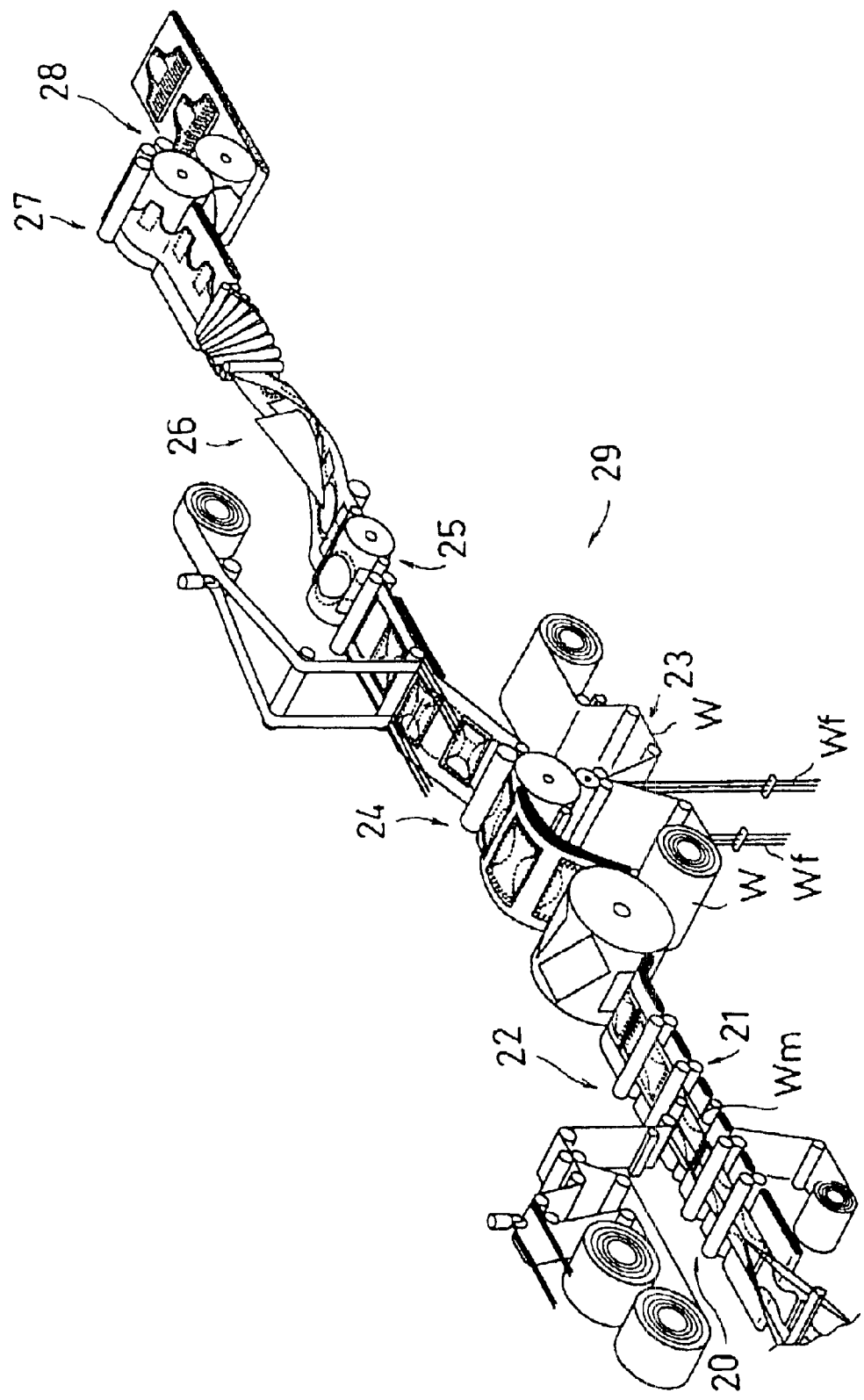
FIG. 9 illustrates an example of a production apparatus for producing an article.

The second embodiment will now be described. FIG. 9 is a diagram illustrating an example of a production apparatus for producing an article. Specifically, a production apparatus 29 is capable of producing a pants-type diaper, which is a type of a worn article.

The production apparatus 29 includes a first cutter unit 20 for cutting the mat Wm, a first seal unit 21 for sealing an end of a combined member obtained by combining a cut-off mat with another web placed thereon, a second cutter unit 22 for cutting along a line between the sealed portions, and a guide unit 23 for guiding and introducing the elastic member Wf between the webs W.

The production apparatus 29 further includes a second seal unit 24 for sealing the web W, onto which the elastic member Wf has been introduced, and the combined member together, a trim cutter unit 25 for opening a leg hole, etc., in the sealed web, a folding unit 26 for folding the web with the hole opened therein, a third seal unit 27 for sealing a boundary of the semi-finished product, and a third cutter unit 28 for cutting along a line between the sealed portions to obtain a cut-off article.

At least one of the first to third cutter units 20, 22 and 28, the first to third seal units 21, 24 and 27 and the trim cutter unit 25 includes a velocity-variable rotating member as described above. Therefore, for a unit having the velocity-variable rotating member, it is not necessary to replace the rotating member even when the size of article is changed.

Figure 10:
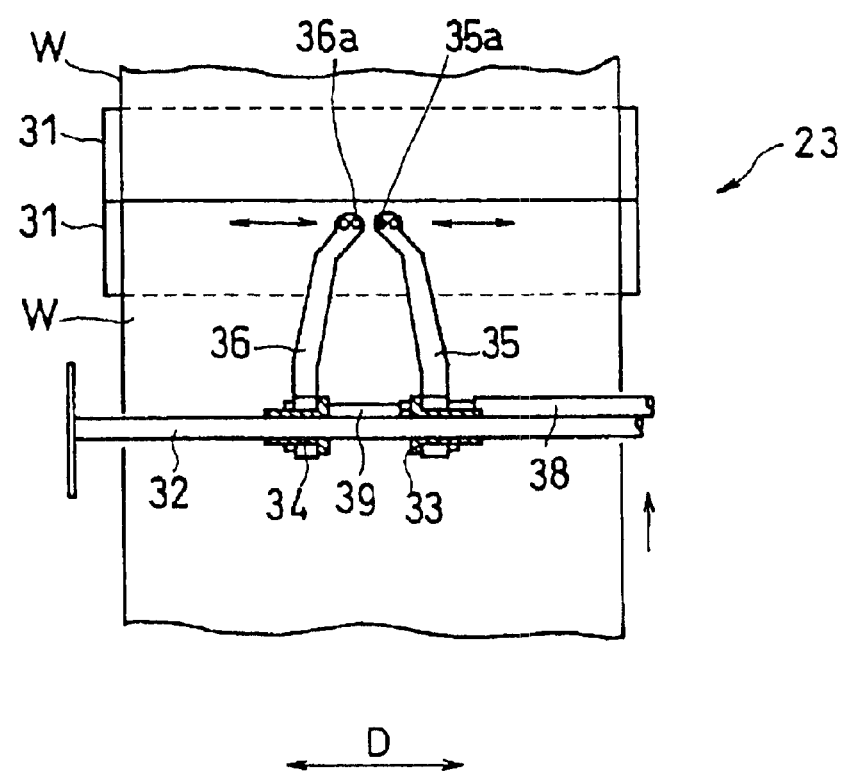
FIG. 10 and FIG. 11 each illustrate an example of a guide unit.

FIG. 10 illustrates an example of the guide unit 23. The guide unit 23 includes a guide shaft 32, first and second sliders 33 and 34 movable along the guide shaft 32, a first guide section 35 provided on the first slider 33, and a second guide section 36 provided on the second slider 34.

The first slider 33 moves along the guide shaft 32 as a shaft 38 reciprocates, and the second slider 34 moves along the guide shaft 32 as a shaft 39 reciprocates. Note that the shaft 38 may be hollow, with the shaft 39 reciprocating in the shaft 38. For such a reciprocation of the shafts 38 and 39, it is necessary to convert the rotation of a motor to a reciprocation. For example, a rotation may be converted to a reciprocation by using a crank mechanism. Alternatively, a rotation may be converted to a reciprocation by using a mechanism such as a ball screw.

The guide sections 35 and 36 reciprocate generally in the axis line direction of a nip roll 31, and places the elastic member Wf at a predetermined position on the web. Thus, the elastic member Wf can be placed at the intended position by the operation of the guide sections 35 and 36.

The pair of nip rolls 31 and 31 sandwich at least one web W and the elastic member Wf, which is led through lead-through sections 35a and 36a located generally at the tips of the first and second guide sections 35 and 36, respectively. It is preferred that the lead-through sections 35a and 36a are arranged in the vicinity of the pair of nip rolls 31 and 31. An adhesive is applied intermittently or continuously on at least one web W. The radius of at least one of the nip rolls 31 and 31 may be 10 mm to 60 mm.

Note that the sliders 33 and 34 move along the same path in the guide unit 23 illustrated in FIG. 10, whereby the sliders 33 and 34 cannot cross each other. However, the lead-through sections 35a and 36a can be moved by the guide sections 35 and 36 along different paths, whereby the lead-through sections 35a and 36a can be crossed each other.

If the sliders 33 and 34 are reciprocated by using a mechanical element such as a cam mechanism, the cam needs to be replaced each time the size of article is changed. However, the sliders 33 and 34 can be reciprocated by a motor as described above, whereby it is possible to control the positions of the sliders 33 and 34 by using the control system 59, 69, thus eliminating the need to replace the cam when the size of article is changed.

Figure 11:
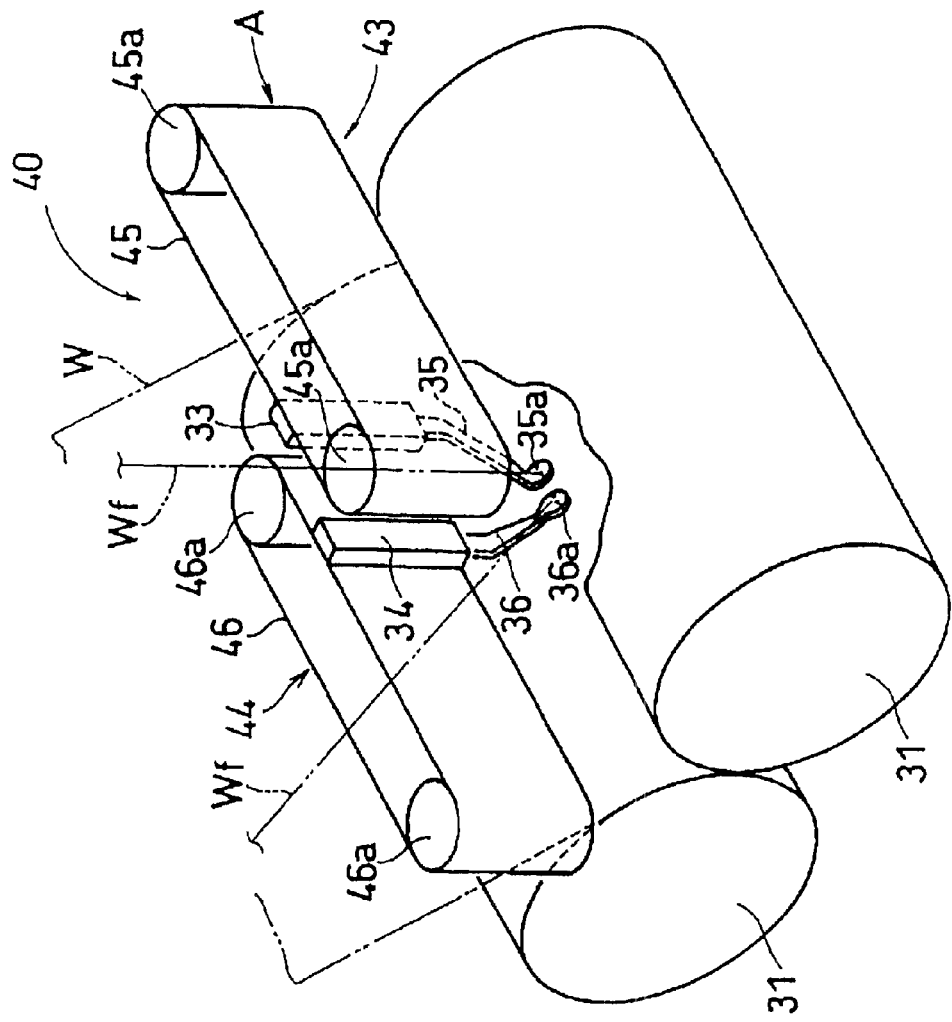

Moreover, a guide unit 40 as illustrated in FIG. 11 may be used instead of the guide unit 23 illustrated in FIG. 10.

Figure 12:
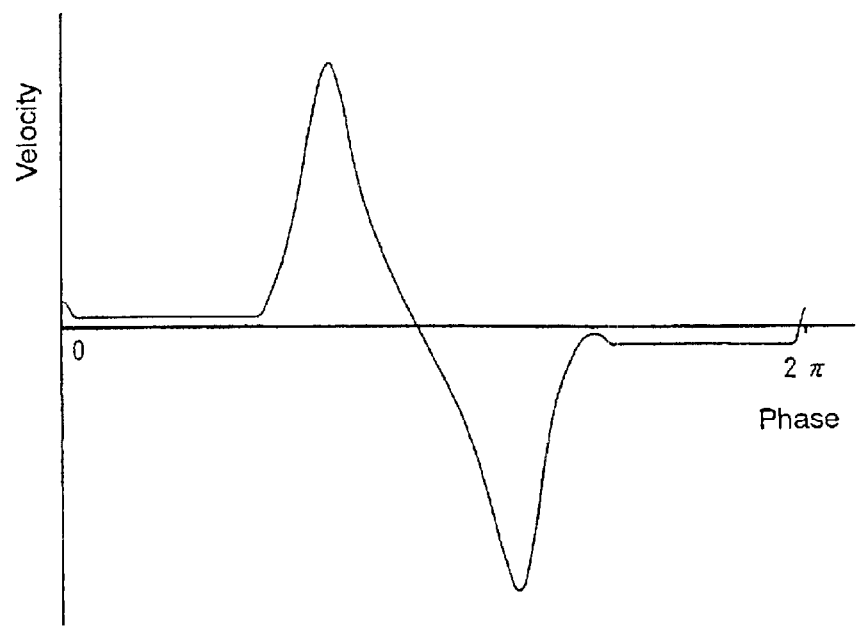
FIG. 12 illustrates an example of the relationship between the velocity of a first guide section and the cycle in which the first guide section places an elastic member in a section.

The guide unit 40 includes a first attachment section 43 and a second attachment section 44. The first attachment section 43 includes a pair of pulleys 45a, a belt 45 wound around the pair of pulleys 45a, and the first guide section 35 for guiding at least one elastic member Wf to the vicinity of a position where the nip rolls 31 and 31 contact each other. The second attachment section 44 includes a pair of pulleys 46a, a belt 46 wound around the pair of pulleys 46a, and the second guide section 36 for guiding at least one elastic member Wf to the vicinity of a position where the nip rolls 31 and 31 contact each other. At least one of the pair of pulleys 45a is rotated by a servo motor (not shown). Similarly, at least one of the pair of pulleys 46a is rotated by a servo motor (not shown). By the rotation of the servo motors, the first and second attachment sections 43 and 44 respectively reciprocate the first and second guide sections 35 and 36 in the width direction of the web W. An example of the relationship between the velocity of the first guide section 35 and one cycle in which the first guide section 35 places the elastic member Wf to a section is illustrated in FIG. 12. In FIG. 12, the maximum/minimum velocity of the first and second guide sections 35 and 36 is about ±10 m/s. Since the maximum/minimum velocity varies depending on the type of servo motor, the maximum/minimum velocity may be set to be about ±20 m/s depending on the type of the servo motor, etc.

Also with the guide unit 40, the first and second attachment sections 43 and 44 can be controlled by the control system 59, 69, thereby eliminating the need to replace a cam when the size of article is changed. Note that the rotational velocity and the phase of the servo motor may be corrected based on the expansion/contraction information as described above.

Third Embodiment

Figure 16:
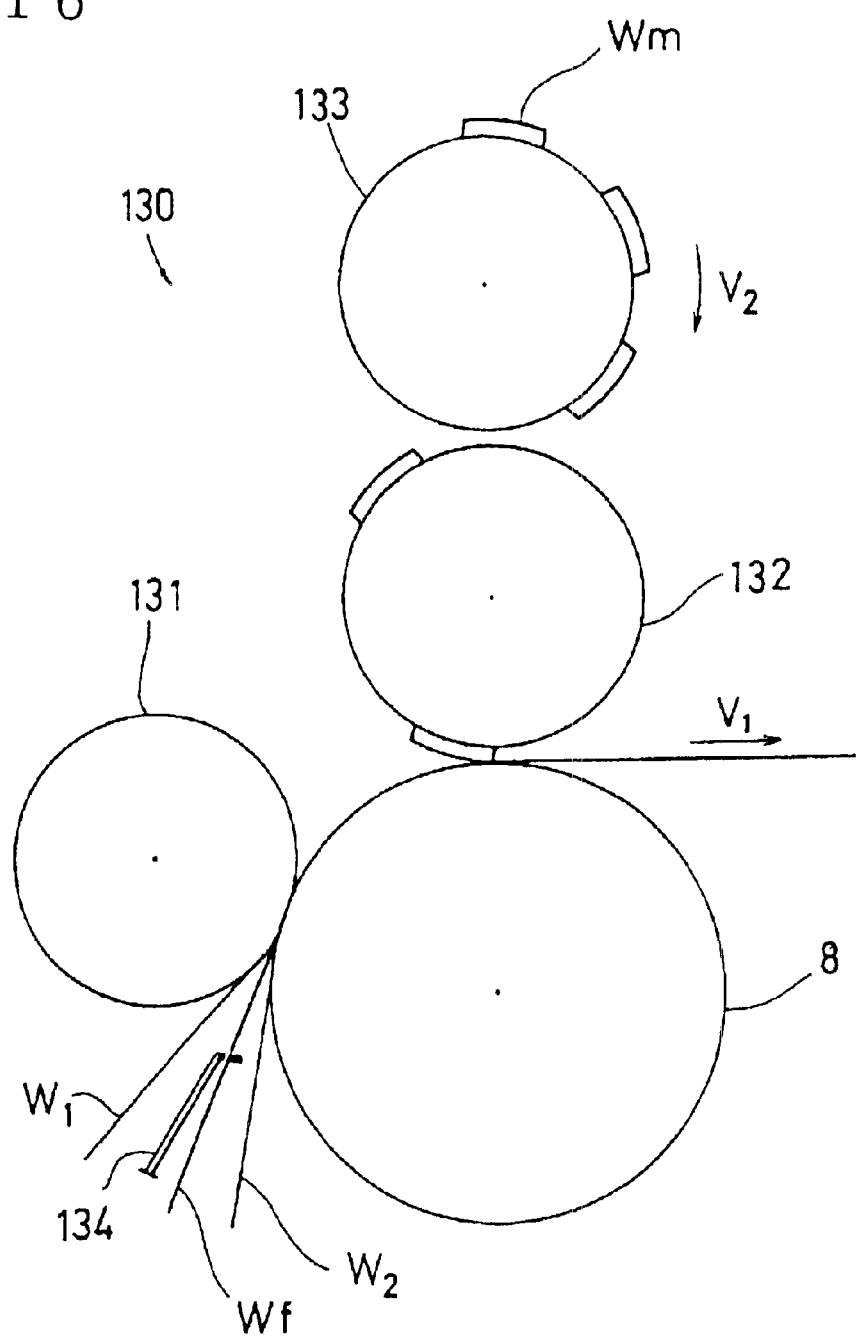
FIG. 16 illustrates an example of a production apparatus for producing an article.

The third embodiment will now be described. FIG. 16 is a diagram illustrating an example of a production apparatus for producing an article.

An apparatus 130 includes a guide section 134 for guiding the elastic member Wf between webs $W_1$ and $W_2$, a nip roll 131 and the assembly drum 8 for sandwiching and adhering the elastic member Wf between the webs $W_1$ and $W_2$, and a re-pitching drum 132 for receiving the mats Wm from a transfer section 133 and changing the interval between the mats Wm. On the assembly drum 8, the mat Wm is placed on the webs $W_1$ and $W_2$, in which the elastic member Wf has been placed in a predetermined shape. An adhesive is applied intermittently or continuously on at least one of the webs $W_1$ and $W_2$. Note that the nip roll 131 has a diameter that is smaller than that of the assembly drum 8 holding the web $W_2$ thereon. Moreover, if the nip roll 131 has a peelability to the adhesive, it is possible to omit the web $W_1$, thereby reducing the cost of the article. Moreover, also in the first and second embodiments described above, an elastic member may be arranged on one web. In such a case, it is preferred that at least one nip roll has a peelability to an adhesive. Moreover, an elastic member such as a rubber may be wound around the nip roll in the first to third embodiments. Moreover, the nip rolls may be designed so that the nip rolls can be moved away from each other for maintenance of the nip rolls.

Where the circumferential velocity of the assembly drum 8 is denoted as $v_1$ and the circumferential velocity of the transfer section 133 as $v_2$, it is preferred that the re-pitching drum 132 receives the mat Wm approximately at the velocity of $v_2$ and releases the mat Wm approximately at the velocity of $v_1$. One or both of the re-pitching drum 132 and the transfer section 133 may adsorb the mat Wm onto the surface of the drum through suction.

Figure 17:
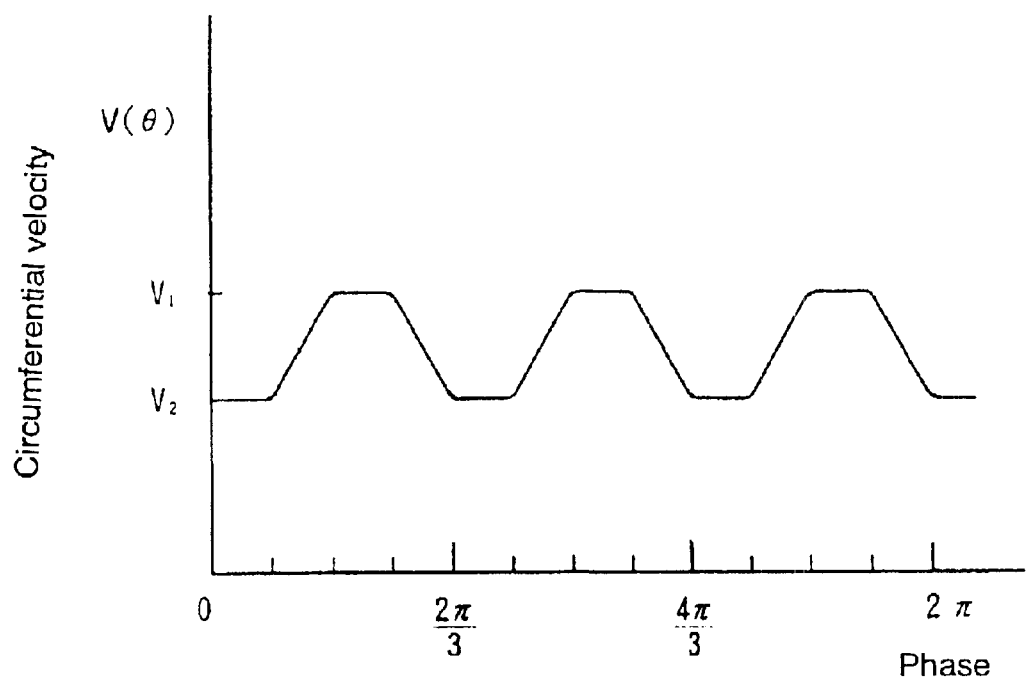
FIG. 17 illustrates an example of the relationship between the phase and the rotational velocity of a re-pitching drum.

FIG. 17 illustrates an example of how the rotational velocity of the re-pitching drum 132 is changed during one revolution of the re-pitching drum 132. When the re-pitching drum 132 receives the mat Wm in a second working area (an area where the re-pitching drum receives a member) that is located in the vicinity of the transfer section 133, the circumferential velocity of the re-pitching drum 132 is set to be generally equal to $v_2$. When the re-pitching drum 132 hands over the mat Wm in a first working area (an area where the re-pitching drum hands over a member) that is located in the vicinity of the assembly drum 8, the circumferential velocity of the re-pitching drum 132 is set to be generally equal to $v_1$. In the example illustrated in FIG. 17, three cycles of operation are performed during one revolution of the re-pitching drum.

By the use of the re-pitching drum 132 as described above, it is possible to change the interval between members. Therefore, it is possible to place the mat Wm, etc., at a predetermined position even if the size of article is changed. Note that the re-pitching drum 132 may be controlled by the control system 59, 69. Moreover, the guide section 134 can be used with any size as it can be controlled by the control system 59, 69 even if the size of article is changed. Moreover, in a case where a mat, which is a semi-finished product, is contracted, the re-pitching drum 132 may receive the mat at a velocity that is greater than the circumferential velocity of the transfer section 133. The contraction of the semi-finished product can be corrected by such a change in the circumferential velocity of the re-pitching drum.

While preferred embodiments of the present invention have been described above with reference to the drawings, various obvious changes and modifications will readily occur to those skilled in the art who read the present specification.

For example, the rotating member of the first to third embodiments may be coupled to a rotating member via a decelerator or accelerator such as a gear.

Moreover, laser cutters may be provided in a guide section, as cutters for forming the leg hole, and the cutters may be controlled according to the size as are the guide sections described above.

Specifically, laser cutters may be provided in place of the arms 35 and 36 illustrated in FIG. 10 and FIG. 11, for example. In a case where a hole is opened in a web by using two guide sections, a problem arises as to the positional alignment at the start and/or the end of the cutting process. For example, by operating the laser cutters so that they are crossed each other at the start and/or the end of the cutting process. Moreover, a hole of a predetermined size may be opened in advance, and the hole is used as the start and/or end position of the cutting process, in which case it is possible to prevent mis-cutting. In such a case, it is preferred that the hole of the predetermined size is smaller than the hole to be cut open by laser and larger than the possible error that may occur when two laser cutters are aimed at one position. While the use of laser cutters has been described, a similar configuration as that for the laser cutters may be employed with other types of cutters such as water jet cutters or hot air cutters.

Thus, such changes and modifications shall fall within the scope of the present invention, which is defined by the appended claims.

A production method of the present invention for producing an article is capable of changing the circumferential velocity of a rotating member according to the size of a semi-finished product during one cycle for machining the semi-finished product. Therefore, it is possible to minimize the need for replacing units including the rotating member.

When a machining section performs a machining process on the semi-finished product, the circumferential velocity of the rotating member can be set to a predetermined velocity, whereby it is possible to perform a desirable machining process on the semi-finished product.

Another production method of the present invention for producing an article is capable of adjusting the position at which a semi-finished product is machined based on the expansion/contraction of the semi-finished product. In other words, the production method of the present invention for producing an article is capable of correcting the time at which a machining section reaches a working area based on the expansion/contraction of the semi-finished product. Therefore, it is possible to perform a machining process on an intended portion of the semi-finished product even if the semi-finished product expands/contracts.

Still another production method of the present invention for producing an article is capable of correcting the circumferential velocity of the rotating member in a working area based on the expansion/contraction of the semi-finished product. Therefore, even if the semi-finished product expands/contracts, it is possible to correct the size of the area to be machined according to the expansion/contraction of the semi-finished product.

Still another production method of the present invention for producing an article is capable of correcting the phase and the circumferential velocity of a rotating member in a working area based on the expansion/contraction of a semi-finished product. Therefore, even if the semi-finished product expands/contracts, it is possible to correct the position to be machined and the size of the area to be machined according to the expansion/contraction of the semi-finished product.

What is claimed is:

1. A production method for producing an article, comprising the step of rotating a rotating member so as to machine a semi-finished product with a machining section included in the rotating member, wherein a circumferential velocity of the rotating member is changed according to a size of the semi-finished product during one cycle in which the semi-finished product is machined.

2. A production method for producing an article according to claim 1, wherein the size of the semi-finished product is a length of the semi-finished product in a flow direction.

3. A production method for producing an article according to claim 1, wherein the size of the semi-finished product is determined as a distance between boundaries between the semi-finished products.

4. A production method for producing an article according to claim 1, wherein the circumferential velocity of the rotating member in a working area is set to be equal to or greater than a velocity that is approximate to a flow velocity of the semi-finished product of a first size.

5. A production method for producing an article according to claim 1, wherein:
   in a case where a semi-finished product of a first size is machined by the rotating member, an average circumferential velocity of the rotating member in a working area is generally the same as an average circumferential velocity of the rotating member in a non-working area; and
   in a case where a length of a semi-finished product of a second size in a flow direction is less than that of the semi-finished product of the first size, the average circumferential velocity of the rotating member in the non-working area is higher than a flow velocity of the semi-finished product of the second size.

6. A production method for producing an article according to claim 1, wherein:
   in a case where a semi-finished product of a first size is machined by the rotating member, an average circumferential velocity of the rotating member in a working area is generally the same as an average circumferential velocity of the rotating member in a non-working area; and
   in a case where the length of the semi-finished product of a second size in the flow direction is greater than that of the semi-finished product of the first size, the average circumferential velocity is lower than the flow velocity.

7. A production method for producing an article according to claim 1, further comprising:
   a hole making step of cutting off an area of a web that is to be a leg hole;
   a preparation step of preparing an absorbent;
   a placement step of placing the absorbent on the web; and
   a cutting step of cutting the web on which the absorbent has been placed, wherein:
   in the hole making step, a cutter, which is the machining section of the rotating member, cuts off the area in a working area by rotating the rotating member; and
   an average circumferential velocity of the rotating member in the working area is different from an average circumferential velocity of the rotating member in a non-working area.

8. A production method for producing an article according to claim 7, further comprising an interval changing step of changing an interval between the absorbents by rotating another rotating member for transferring the absorbents while changing a circumferential velocity thereof according to the size of the absorbents before the prepared absorbents are placed on the web.

9. A production method for producing an article according to claim 8, further comprising:
   a detection step of detecting a velocity signal containing velocity information regarding a velocity of the semi-finished product;
   a production step of producing an interval signal in response to a specified portion of the semi-finished product passing through a predetermined point;
   a calculation step of calculating an expansion/contraction of the semi-finished product based on a velocity signal that is measured between the interval signals and a reference that is issued between the interval signals; and
   a step of correcting at least one of a circumferential velocity of the other rotating member and a phase thereof based on the expansion/contraction.

10. A production method for producing an article according to claim 8, further comprising the step of correcting at least one of a circumferential velocity of the other rotating member and a phase thereof based on the expansion/contraction of the semi-finished product.

11. A production method for producing an article according to claim 7, further comprising the step of placing an elastic member on the web by rotating another rotating member for reciprocating a guide section for guiding the elastic member while changing a circumferential velocity thereof according to the size of the semi-finished product.

12. A production method for producing an article according to claim 11, further comprising the step of correcting at least one of a circumferential velocity of the other rotating member and a phase thereof based on the expansion/contraction of the semi-finished product.

13. A production method for producing an article according to claim 11, further comprising:
   a detection step of detecting a velocity signal containing velocity information regarding a velocity of the semi-finished product;
   a production step of producing an interval signal in response to a specified portion of the semi-finished product passing through a predetermined point;
   a calculation step of calculating an expansion/contraction of the semi-finished product based on a velocity signal that is measured between the interval signals and a reference that is issued between the interval signals; and
   a step of correcting at least one of a circumferential velocity of the other rotating member and a phase thereof based on the expansion/contraction.

14. A production method for producing an article according to claim 1, further comprising:
   a hole making step of cutting off an area of a web that is to be a leg hole;
   a preparation step of preparing an absorbent;
   a placement step of placing the absorbent on the web; and
   a cutting step of cutting the web on which the absorbent has been placed, wherein:
   in the preparation step, a cutter, which is the machining section of the rotating member, cuts a continuous absorbent sheet in a working area by rotating the rotating member, thereby preparing the absorbent; and
   an average circumferential velocity of the rotating member in the working area is different from an average circumferential velocity of the rotating member in a non-working area.

15. A production method for producing an article according to claim 14, further comprising the step of placing an elastic member on the web by rotating another rotating member for reciprocating a guide section for guiding the elastic member while changing a circumferential velocity thereof according to the size of the semi-finished product.

16. A production method for producing an article according to claim 14, further comprising the step of correcting a time at which the machining section reaches the working area based on an expansion/contraction of the semi-finished product.

17. A production method for producing an article according to claim 14, further comprising the step of correcting a position at which the semi-finished product is machined based on an expansion/contraction of the semi-finished product.

18. A production method for producing an article according to claim 14, further comprising the step of correcting a circumferential velocity of the machining section in a working area based on an expansion/contraction of the semi-finished product.

19. A production method for producing an article according to claim 14, further comprising an interval changing step of changing an interval between the absorbents by rotating another rotating member for transferring the absorbents while changing a circumferential velocity thereof according to the size of the absorbents before the prepared absorbents are placed on the web.

20. A production method for producing an article according to claim 1, further comprising:
   a hole making step of cutting off an area of a web that is to be a leg hole;
   a preparation step of preparing an absorbent;
   a placement step of placing the absorbent on the web; and
   a cutting step of cutting the web on which the absorbent has been placed, wherein:
   in the cutting step, a cutter, which is the machining section of the rotating member, cuts the web in a working area by rotating the rotating member; and
   an average circumferential velocity of the rotating member in the working area is different from an average circumferential velocity of the rotating member in a non-working area.

21. A production method for producing an article according to claim 20, further comprising an interval changing step of changing an interval between the absorbents by rotating another rotating member for transferring the absorbents while changing a circumferential velocity thereof according to the size of the absorbents before the prepared absorbents are placed on the web.

22. A production method for producing an article according to claim 20, further comprising the step of placing an elastic member on the web by rotating another rotating member for reciprocating a guide section for guiding the elastic member while changing a circumferential velocity thereof according to the size of the semi-finished product.

23. A production method for producing an article according to claim 20, further comprising the step of correcting a time at which the machining section reaches the working area based on an expansion/contraction of the semi-finished product.

24. A production method for producing an article according to claim 20, further comprising the step of correcting a position at which the semi-finished product is machined based on an expansion/contraction of the semi-finished product.

25. A production method for producing an article according to claim 20, further comprising the step of correcting a circumferential velocity of the machining section in a working area based on an expansion/contraction of the semi-finished product.

26. A production method for producing an article according to claim 1, further comprising:
   a preparation step of preparing an absorbent;
   a placement step of placing the absorbent on a web;
   a hole making step of cutting off an area of the web that is to be a leg hole; and
   a cutting step of cutting the web on which the absorbent has been placed, wherein:
   in the hole making step, a cutter, which is the machining section of the rotating member, cuts off the area in a working area by rotating the rotating member; and
   an average circumferential velocity of the rotating member in the working area is different from an average circumferential velocity of the rotating member in a non-working area.

27. A production method for producing an article according to claim 26, further comprising an interval changing step of changing an interval between the absorbents by rotating another rotating member for transferring the absorbents while changing a circumferential velocity thereof according to the size of the absorbents before the prepared absorbents are placed on the web.

28. A production method for producing an article according to claim 26, further comprising the step of placing an elastic member on the web by rotating another rotating member for reciprocating a guide section for guiding the elastic member while changing a circumferential velocity thereof according to the size of the semi-finished product.

29. A production method for producing an article according to claim 26, further comprising the step of correcting a time at which the machining section reaches the working area based on an expansion/contraction of the semi-finished product.

30. A production method for producing an article according to claim 26, further comprising the step of correcting a position at which the semi-finished product is machined based on an expansion/contraction of the semi-finished product.

31. A production method for producing an article according to claim 26, further comprising the step of correcting a circumferential velocity of the machining section in a working area based on an expansion/contraction of the semi-finished product.

32. A production method for producing an article according to claim 1, further comprising:
   a preparation step of preparing an absorbent;
   a placement step of placing the absorbent on a web;
   a hole making step of cutting off an area of the web that is to be a leg hole; and
   a cutting step of cutting the web on which the absorbent has been placed, wherein:
   in the preparation step, a cutter, which is the machining section of the rotating member, cuts a continuous absorbent sheet in a working area by rotating the rotating member, thereby preparing the absorbent; and
   an average circumferential velocity of the rotating member in the working area is different from an average circumferential velocity of the rotating member in a non-working area.

33. A production method for producing an article according to claim 32, further comprising an interval changing step of changing an interval between the absorbents by rotating another rotating member for transferring the absorbents while changing a circumferential velocity thereof according to the size of the absorbents before the prepared absorbents are placed on the web.

34. A production method for producing an article according to claim 32, further comprising the step of placing an elastic member on the web by rotating another rotating member for reciprocating a guide section for guiding the elastic member while changing a circumferential velocity thereof according to the size of the semi-finished product.

35. A production method for producing an article according to claim 32, further comprising the step of correcting a time at which the machining section reaches the working area based on an expansion/contraction of the semi-finished product.

36. A production method for producing an article according to claim 32, further comprising the step of correcting a position at which the semi-finished product is machined based on an expansion/contraction of the semi-finished product.

37. A production method for producing an article according to claim 32, further comprising the step of correcting a circumferential velocity of the machining section in a working area based on an expansion/contraction of the semi-finished product.

38. A production method for producing an article according to claim 1, further comprising:
   a preparation step of preparing an absorbent;
   a placement step of placing the absorbent on a web;
   a hole making step of cutting off an area of the web that is to be a leg hole; and
   a cutting step of cutting the web on which the absorbent has been placed, wherein:
   in the cutting step, a cutter, which is the machining section of the rotating member, cuts the web in a working area by rotating the rotating member; and
   an average circumferential velocity of the rotating member in the working area is different from an average circumferential velocity of the rotating member in a non-working area.

39. A production method for producing an article according to claim 38, further comprising an interval changing step of changing an interval between the absorbents by rotating another rotating member for transferring the absorbents while changing a circumferential velocity thereof according to the size of the absorbents before the prepared absorbents are placed on the web.

40. A production method for producing an article according to claim 38, further comprising the step of placing an elastic member on the web by rotating another rotating member for reciprocating a guide section for guiding the elastic member while changing a circumferential velocity thereof according to the size of the semi-finished product.

41. A production method for producing an article according to claim 38, further comprising the step of correcting a time at which the machining section reaches the working area based on an expansion/contraction of the semi-finished product.

42. A production method for producing an article according to claim 38, further comprising the step of correcting a position at which the semi-finished product is machined based on an expansion/contraction of the semi-finished product.

43. A production method for producing an article according to claim 38, further comprising the step of correcting a circumferential velocity of the machining section in a working area based on an expansion/contraction of the semi-finished product.

44. A production method for producing an article according to claim 1, further comprising the step of handing over the semi-finished products while changing an interval between the semi-finished products by rotating another rotating member for transferring received semi-finished products while changing a circumferential velocity thereof according to the size of the semi-finished products.

45. A production method for producing an article according to claim 44, further comprising the step of correcting at least one of a circumferential velocity of the other rotating member and a phase thereof based on the expansion/contraction of the semi-finished product.

46. A production method for producing an article according to claim 44, further comprising:
   a detection step of detecting a velocity signal containing velocity information regarding a velocity of the semi-finished product;
   a production step of producing an interval signal in response to a specified portion of the semi-finished product passing through a predetermined point;
   a calculation step of calculating an expansion/contraction of the semi-finished product based on a velocity signal that is measured between the interval signals and a reference that is issued between the interval signals; and
   a step of correcting at least one of a circumferential velocity of the other rotating member and a phase thereof based on the expansion/contraction.

47. A production method for producing an article according to claim 1, further comprising the step of correcting a time at which the machining section reaches the working area based on an expansion/contraction of the semi-finished product.

48. A production method for producing an article according to claim 1, further comprising:
   a detection step of detecting a velocity signal containing velocity information regarding a velocity of the semi-finished product;
   a production step of producing an interval signal in response to a specified portion of the semi-finished product passing through a predetermined point;
   a step of producing a timing signal when a predetermined number of velocity signals are counted after issuance of the interval signal; and
   a step of correcting a position at which the semi-finished product is machined based on the timing signal.

49. A production method for producing an article according to claim 1, further comprising:
   a detection step of detecting a velocity signal containing velocity information regarding a velocity of the semi-finished product;
   a production step of producing an interval signal in response to a specified portion of the semi-finished product passing through a predetermined point;
   a step of producing a timing signal when a predetermined amount of time passes after issuance of the interval signal; and
   a step of correcting a position at which the semi-finished product is machined based on the timing signal.

50. A production method for producing an article according to claim 1, further comprising the step of correcting a position at which the semi-finished product is machined based on an expansion/contraction of the semi-finished product.

51. A production method for producing an article according to claim 1, further comprising:
   a detection step of detecting a velocity signal containing velocity information regarding a velocity of the semi-finished product;
   a production step of producing an interval signal in response to a specified portion of the semi-finished product passing through a predetermined point;
   a calculation step of calculating an expansion/contraction of the semi-finished product based on the number of pulses of a velocity signal that is measured between the interval signals and the number of pulses of a reference velocity signal that is issued between the interval signals;
   a step of correcting a predetermined number based on the expansion/contraction;
   a step of producing a timing signal when the corrected predetermined number of velocity signals are counted after issuance of the interval signal; and a step of correcting a position at which the semi-finished product is machined based on the timing signal.

52. A production method for producing an article according to claim 1, further comprising:

a detection step of detecting a velocity signal containing velocity information regarding a velocity of the semi-finished product;

a production step of producing an interval signal in response to a specified portion of the semi-finished product passing through a predetermined point;

a calculation step of calculating an expansion/contraction of the semi-finished product based on the number of pulses of a velocity signal that is measured between the interval signals and the number of pulses of a reference velocity signal that is issued between the interval signals;

a step of correcting a predetermined amount of time based on the expansion/contraction;

a step of producing a timing signal when the corrected predetermined amount of time passes after issuance of the interval signal; and a step of correcting a position at which the semi-finished product is machined based on the timing signal.

53. A production method for producing an article according to claim 1, further comprising the step of correcting a circumferential velocity of the machining section in a working area based on an expansion/contraction of the semi-finished product.

54. A production method for producing an article according to claim 1, further comprising:

a detection step of detecting a velocity signal containing velocity information regarding a velocity of the semi-finished product;

a production step of producing an interval signal in response to a specified portion of the semi-finished product passing through a predetermined point;

a calculation step of calculating an expansion/contraction of the semi-finished product based on the number of velocity signals that are measured between the interval signals and the number of reference velocity signals that are issued between the interval signals; and a step of correcting a circumferential velocity of the machining section in a working area based on the expansion/contraction.

55. A production method for producing an article according to claim 1, further comprising the steps of:

cutting a member by a cutter roll into pieces of a predetermined length;

transferring the cut members by a transfer section of the transfer roll;

attaching the cut members on a web at a first interval by the transfer roll and a protrusion of a press roll, wherein:

the press roll rotates as the rotating member, and the protrusion attaches the members on the web; and an average circumferential velocity of the transfer roll in a working area is different from that in a non-working area.

56. A production method for producing an article according to claim 55, further comprising the step of correcting at least one of a circumferential velocity of the press roll and a phase thereof in the working area based on an expansion/contraction of the web.

57. A production method for producing an article, comprising the step of rotating a rotating member so as to machine a semi-finished product with a machining section included in the rotating member and the step of correcting at least one of a phase of the rotating member and a circumferential velocity thereof in a working area based on an expansion/contraction of the semi-finished product.

* * * * *